United States Patent [19]

Cordell

[11] Patent Number: 5,387,742
[45] Date of Patent: Feb. 7, 1995

[54] TRANSGENIC MICE DISPLAYING THE AMYLOID-FORMING PATHOLOGY OF ALZHEIMER'S DISEASE

[75] Inventor: Barbara Cordell, Palo Alto, Calif.

[73] Assignee: Scios Nova Inc., Mountain View, Calif.

[21] Appl. No.: 716,725

[22] Filed: Jun. 17, 1991

Related U.S. Application Data

[63] Continuation-in-part of Ser. No. 538,857, Jun. 15, 1990, abandoned.

[51] Int. Cl.$^6$ .................. A61K 49/00; C12N 15/00; C07H 15/12
[52] U.S. Cl. ............................ 800/2; 424/9; 435/142.3; 536/23.5
[58] Field of Search .................. 800/2; 435/6; 514/44

[56] References Cited

FOREIGN PATENT DOCUMENTS

| 0451700 | 10/1991 | European Pat. Off. |
| WO89/06689 | 7/1989 | WIPO |
| WO89/06693 | 7/1989 | WIPO |
| WO92/06187 | 4/1992 | WIPO |
| WO93/02189 | 2/1993 | WIPO |

OTHER PUBLICATIONS

Heideman, Transgenic Rats: A Discussion in Transgenic Animals: Proceedings of the Symposium on Transgenic Technology in Medicine and Agriculture. NIH1988, Boston: Butterworth-Heinemann, 1991, pp. 325–332.
Armstrong et al (1988) Biology of Reprod. 39, 511–518.
Jucher et al (1992) Science 255, 1443–1445.
Dyrks et al (1988) EMBO J. 7, 949–957.
Sakimura et al (1987) Gene 60, 103–113.
Ponte et al (1988) Nature 331, 525–527.
Palmiter (1986) Ann. Rev. Genet. 20, 465–499.
Kang et al (1987) Nature, 325, 733–736.
Kitaguchi et al (1988) Nature 331, 530–532.
Swanson et al (1985) Nature 317, 363–366.
Masters et al (1985) Proc. Natl. Acad. Sci 82, 4245–4249.
Quon et al. "Formation of $\beta$-amyloid Protein Deposits in Brains of Transgenic Mice" *Nature* (1991) 352:239–241.

*Primary Examiner*—Elizabeth C. Weimar
*Assistant Examiner*—Deborah Crouch
*Attorney, Agent, or Firm*—Morrison & Foerster

[57] ABSTRACT

Cloned recombinant or synthetic DNA sequences related to the pathology of Alzheimer's disease are injected into fertilized mouse eggs. The injected eggs are implanted in pseudo pregnant females and are grown to term to provide transgenic mice whose cells express proteins related to the pathology of Alzheimer's disease. The injected sequences are constructed having promoter sequences connected so as to express the desired protein in brain tissues of the transgenic mouse. The proteins which are preferably ubiquitously expressed include (1) $\beta$-amyloid core precursor proteins; and (2) $\beta$-amyloid related precursor proteins; and (3) serine protease inhibitor. The transgenic mice provide useful models for studying compounds being tested for their usefulness in treating Alzheimer's disease, and for studying the in vivo interrelationships of these proteins to each other.

4 Claims, 38 Drawing Sheets

FIG 1A

```
ATG CTG CCC GGT TTG GCA CTG CTC CTG CTG GCC GCC TGG ACG GCT CGG        48
Met Leu Pro Gly Leu Ala Leu Leu Leu Leu Ala Ala Trp Thr Ala Arg
  1               5                  10                  15

GCG CTG GAG GTA CCC ACT GAT GGT AAT GCT GGC CTG CTG GCT GAA CCC        96
Ala Leu Glu Val Pro Thr Asp Gly Asn Ala Gly Leu Leu Ala Glu Pro
             20                  25                  30

CAG ATT GCC ATG TTC TGT GGC AGA CTG AAC ATG CAC ATG AAT GTC CAG       144
Gln Ile Ala Met Phe Cys Gly Arg Leu Asn Met His Met Asn Val Gln
         35                  40                  45

AAT GGG AAG TGG GAT TCA GAT CCA TCA GGG ACC AAA ACC TGC ATT GAT       192
Asn Gly Lys Trp Asp Ser Asp Pro Ser Gly Thr Lys Thr Cys Ile Asp
     50                  55                  60

ACC AAG GAA GGC ATC CTG CAG TAT TGC CAA GAA GTC TAC CCT GAA CTG       240
Thr Lys Glu Gly Ile Leu Gln Tyr Cys Gln Glu Val Tyr Pro Glu Leu
 65                  70                  75                  80

CAG ATC ACC AAT GTG GTA GAA GCC AAC CAA CCA GTG ACC ATC CAG AAC       288
Gln Ile Thr Asn Val Val Glu Ala Asn Gln Pro Val Thr Ile Gln Asn
                 85                  90                  95

TGG TGC AAG CGG GGC CGC AAG CAG TGC AAG ACC CAT CCC CAC TTT GTG       336
Trp Cys Lys Arg Gly Arg Lys Gln Cys Lys Thr His Pro His Phe Val
            100                 105                 110
```

| ATT | CCC | TAC | CGC | TGC | TTA | GTT | GGT | GAG | TTT | GTA | AGT | GAT | GCC | CTT | CTC | 384 |
|---|---|---|---|---|---|---|---|---|---|---|---|---|---|---|---|---|
| Ile | Pro | Tyr | Arg | Cys | Leu | Val | Gly | Glu | Phe | Val | Ser | Asp | Ala | Leu | Leu | |
| | 115 | | | | | | 120 | | | | | 125 | | | | |

| GTT | CCT | GAC | AAG | TGC | AAA | TTC | TTA | CAC | CAG | GAG | AGG | ATG | GAT | GTT | TGC | 432 |
|---|---|---|---|---|---|---|---|---|---|---|---|---|---|---|---|---|
| Val | Pro | Asp | Lys | Cys | Lys | Phe | Leu | His | Gln | Glu | Arg | Met | Asp | Val | Cys | |
| 130 | | | | | | 135 | | | | | 140 | | | | | |

| GAA | ACT | CAT | CTT | CAC | TGG | CAC | ACC | GTC | GCC | AAA | GAG | ACA | TGC | AGT | GAG | 480 |
|---|---|---|---|---|---|---|---|---|---|---|---|---|---|---|---|---|
| Glu | Thr | His | Leu | His | Trp | His | Thr | Val | Ala | Lys | Glu | Thr | Cys | Ser | Glu | |
| 145 | | | | | 150 | | | | | 155 | | | | | 160 | |

| AAG | AGT | ACC | AAC | TTG | CAT | GAC | TAC | GGC | ATG | TTG | CTG | CCC | TGC | GGA | ATT | 528 |
|---|---|---|---|---|---|---|---|---|---|---|---|---|---|---|---|---|
| Lys | Ser | Thr | Asn | Leu | His | Asp | Tyr | Gly | Met | Leu | Leu | Pro | Cys | Gly | Ile | |
| | | | 165 | | | | | 170 | | | | | 175 | | | |

| GAC | AAG | TTC | CGA | GGG | GTA | GAG | TTT | GTG | TGT | TGC | CCA | CTG | GCT | GAA | GAA | 576 |
|---|---|---|---|---|---|---|---|---|---|---|---|---|---|---|---|---|
| Asp | Lys | Phe | Arg | Gly | Val | Glu | Phe | Val | Cys | Cys | Pro | Leu | Ala | Glu | Glu | |
| | | | 180 | | | | | 185 | | | | | 190 | | | |

| AGT | GAC | AAT | GTG | GAT | TCT | GCT | GAT | GCG | GAG | GAG | GAT | GAC | TCG | GAT | GTC | 624 |
|---|---|---|---|---|---|---|---|---|---|---|---|---|---|---|---|---|
| Ser | Asp | Asn | Val | Asp | Ser | Ala | Asp | Ala | Glu | Glu | Asp | Asp | Ser | Asp | Val | |
| | | 195 | | | | | 200 | | | | | 205 | | | | |

```
TGG TGG GGC GGA GCA GAC ACA GAC TAT GCA GAT GGG AGT GAA GAC AAA    672
Trp Trp Gly Gly Ala Asp Thr Asp Tyr Ala Asp Gly Ser Glu Asp Lys
210                     215                 220

GTA GAA GTA GCA GAG GAA GAA GTG GCT GAG GTG GAA GAA    720
Val Glu Val Ala Glu Glu Glu Val Ala Glu Val Glu Glu
225                 230                 235                 240

GAA GCC GAT GAT GAC GAG GAT GGT GAT GAG GTA GAG GAA    768
Glu Ala Asp Asp Asp Glu Asp Gly Asp Glu Val Glu Glu
        245                 250                 255

GAG GCT GAG GAA CCC TAC GAA CAA GCC GAA GAA AGA ACC ACC AGC ATT    816
Glu Ala Glu Glu Pro Tyr Glu Gln Ala Glu Glu Arg Thr Thr Ser Ile
            260                 265                 270

GCC ACC ACC ACC ACC ACA GAG TCT GTG GAA GAG GTG GTT CGA    864
Ala Thr Thr Thr Thr Thr Glu Ser Val Glu Glu Val Val Arg
275                 280                 285

GAG GTG TGC TCT GAA CAA GCC GAG ACG GGG CCG TGC CGA GCA ATG ATC    912
Glu Val Cys Ser Glu Gln Ala Glu Thr Gly Pro Cys Arg Ala Met Ile
            290                 295                 300

TCC CGC TGG TAC TTT GAT GTG ACT GAA GGG AAG TGT GCC CCA TTC TTT    960
Ser Arg Trp Tyr Phe Asp Val Thr Glu Gly Lys Cys Ala Pro Phe Phe
305                 310                 315                 320
```

```
TAC GGC GGA TGT GGC GGC AAC CGG AAC AAC TTT GAC ACA GAA GAG TAC        1008
Tyr Gly Gly Cys Gly Gly Asn Arg Asn Asn Phe Asp Thr Glu Glu Tyr
          325                     330                     335

TGC ATG GCC GTG TGT GGC AGC GCC ATT CCT ACA ACA GCA GCC AGT ACC        1056
Cys Met Ala Val Cys Gly Ser Ala Ile Pro Thr Thr Ala Ala Ser Thr
          340                     345                     350

CCT GAT GCC GTT GAC AAG TAT CTC GAG ACA CCT GGG GAT GAG AAT GAA        1104
Pro Asp Ala Val Asp Lys Tyr Leu Glu Thr Pro Gly Asp Glu Asn Glu
          355                     360                     365

CAT GCC CAT TTC CAG AAA GCC AAA GAG AGG CTT GAG GCC AAG CAC CGA        1152
His Ala His Phe Gln Lys Ala Lys Glu Arg Leu Glu Ala Lys His Arg
          370                     375                     380

GAG AGA ATG TCC CAG GTC ATG AGA GAA TGG GAA GAG GCA GAA CGT CAA        1200
Glu Arg Met Ser Gln Val Met Arg Glu Trp Glu Glu Ala Glu Arg Gln
          385                     390                     395                     400

GCA AAG AAC TTG CCT AAA GCT GAT AAG AAG GCA GTT ATC CAG CAT TTC        1248
Ala Lys Asn Leu Pro Lys Ala Asp Lys Lys Ala Val Ile Gln His Phe
          405                     410                     415

CAG GAG AAA GTG GAA TCT TTG GAA CAG GAA GCA GCC AAC GAG AGA CAG        1296
```

```
Gln Glu Lys Val Glu Ser Leu Glu Gln Glu Ala Ala Asn Glu Arg Gln
            420             425             430
CAG CTG GTG GAG ACA CAC ATG GCC AGA GTG GAA GCC ATG CTC AAT GAC       1344
Gln Leu Val Glu Thr His Met Ala Arg Val Glu Ala Met Leu Asn Asp
        435             440             445
CGC CGC CTG GCC CTG GAG AAC TAC ATC ACC GCT CTG CAG GCT GTT          1392
Arg Arg Arg Leu Ala Leu Glu Asn Tyr Ile Thr Ala Leu Gln Ala Val
    450             455             460
CCT CGG CCT CGT CAC GTG TTC AAT ATG CTA AAG AAG TAT GTC CGC          1440
Pro Arg Pro Arg His Val Phe Asn Met Leu Lys Lys Tyr Val Arg
465             470             475             480
GCA GAA AAG GAC AGA CAG CAC ACC CTA AAG CAT TTC GAG CAT GTG          1488
Ala Glu Lys Asp Arg Gln His Thr Leu Lys His Phe Glu His Val
            485             490             495
CGC ATG GTG GAT CCC AAG AAA GCC GCT CAG ATC CGG TCC CAG GTT ATG       1536
Arg Met Val Asp Pro Lys Lys Ala Ala Gln Ile Arg Ser Gln Val Met
        500             505             510
ACA CAC CTC CGT GTG ATT TAT GAG CGC ATG AAT CAG TCT CTC TCC CTG       1584
Thr His Leu Arg Val Ile Tyr Glu Arg Met Asn Gln Ser Leu Ser Leu
    515             520             525
```

```
CTC TAC AAC GTG CCT GCA GAG GAG ATT CAG GAT GAA GTT GAT                          1632
Leu Tyr Asn Val Pro Ala Glu Glu Ile Gln Asp Glu Val Asp
530                 535             540

GAG CTT CAG AAA GAG CAA AAC TAT TCA GAT GAC GTC TTG GCC AAC                      1680
Glu Leu Gln Lys Glu Gln Asn Tyr Ser Asp Asp Val Leu Ala Asn
545                 550             555             560

ATG ATT AGT GAA CCA AGG ATC AGT TAC GGA AAC GAT GCT CTC ATG CCA                  1728
Met Ile Ser Glu Pro Arg Ile Ser Tyr Gly Asn Asp Ala Leu Met Pro
        565             570             575

TCT TTG ACC GAA ACG AAA ACC ACC GTG GAG CTC CTT CCC GTG AAT GGA                  1776
Ser Leu Thr Glu Thr Lys Thr Thr Val Glu Leu Leu Pro Val Asn Gly
580             585             590

GAG TTC AGC CTG GAC GAT GAT CTC CAG CCG TGG CAT TCT TTT GGG GCT GAC              1824
Glu Phe Ser Leu Asp Asp Asp Leu Gln Pro Trp His Ser Phe Gly Ala Asp
    595             600             605

TCT GTG CCA GCC AAC ACA GAA GAA GTT GAG CCT GTT GAT GCC CGC                      1872
Ser Val Pro Ala Asn Thr Glu Glu Val Glu Pro Val Asp Ala Arg
610             615             620
```

```
CCT GCT GCC GAC CGA GGA CTG ACC ACT CGA CCA GGT TCT GGG TTG ACA
Pro Ala Ala Asp Arg Gly Leu Thr Thr Arg Pro Gly Ser Gly Leu Thr    1920
625                 630                 635                 640

AAT ATC AAG ACG GAG ATC TCT GAA GTG AAG ATG GAT GCA GAA TTC
Asn Ile Lys Thr Glu Ile Ser Glu Val Lys Met Asp Ala Glu Phe        1968
        645                 650                 655

CGA CAT GAC TCA GGA TAT GAA GTT CAT CAA AAA TTG GTG TTC TTT
Arg His Asp Ser Gly Tyr Glu Val His Gln Lys Leu Val Phe Phe        2016
            660                 665                 670

GCA GAA GAT GTG GGT TCA AAC AAA GGT GCA ATC ATT GGA CTC ATG GTG
Ala Glu Asp Val Gly Ser Asn Lys Gly Ala Ile Ile Gly Leu Met Val    2064
                675                 680                 685
```

```
GGC GGT GTT GTC ATA GCG ACA GTG ATC GTC ATC ACC TTG GTG ATG CTG    2112
Gly Gly Val Val Ile Ala Thr Val Ile Val Ile Thr Leu Val Met Leu
690                 695                 700

AAG AAA CAG TAC ACA TCC ATT CAT CAT GGT GTG GAG GTT GAC            2160
Lys Lys Gln Tyr Thr Ser Ile His His Gly Val Glu Val Asp
705                 710                 715                 720

GCC GCT GTC ACC CCA GAG CGC CAC CTG TCC AAG ATG CAG CAG AAC        2208
Ala Ala Val Thr Pro Glu Arg His Leu Ser Lys Met Gln Gln Asn
            725                 730                 735

GGC TAC GAA AAT CCA ACC TAC AAG TTC TTT GAG CAG ATG CAG AAC        2253
Gly Tyr Glu Asn Pro Thr Tyr Lys Phe Phe Glu Gln Met Gln Asn
            740                 745                 750

TAG                                                                 2256
```

```
Asp Ala Glu Phe Arg His Asp Ser Gly Tyr Glu Val His His Gln Lys
 1               5                  10                  15
Leu Val Phe Phe Ala Glu Asp Val Gly Ser Asn Lys Gly Ala Ile Ile
                20                  25                  30
Gly Leu Met Val Gly Gly Val Val Ile Ala Thr Val Ile Val Ile Thr
        35                  40                  45
Leu Val Met Leu Lys Lys Lys Gln Tyr Thr Ser Ile His His Gly Val
    50                  55                  60
Val Glu Val Asp Ala Ala Val Thr Pro Glu Glu Arg His Leu Ser Lys
65                  70                  75                  80
Met Gln Gln Asn Gly Tyr Glu Asn Pro Thr Tyr Lys Phe Pro Glu Gln
                85                  90                  95

Met Gln Asn
```

FIG.3

```
Asp Ala Glu Phe Arg His Asp Ser Gly Tyr Glu Val His His Gln Lys
 1                   5                  10                  15
Leu Val Phe Phe Ala Glu Asp Val Gly Ser Asn Lys Gly Ala Ile Ile
                    20                  25                  30
Gly Leu Met Val Gly Gly Val Val Ile Ala
                    35                  40
```

Sequence around ATG:

MT promoter    CCAGATCTGGAA<u>ATG</u>

```
TIHUBI: Inter-alpha-trypsin inhibitor (BPI type)
        50.0% identity in 52 aa overlap 1"  AVLPQEKEGSGGGQLVTEVTKKEDSCQLGYSAGPCMGMTSRYFYNGTSMACETFQYGGCM
INSERT    1'                                  EVCSEQAETGPCRAMISRWYFDVTEGKCAPFFYGGCGGNRN
                                              : . . : : : : : : . .  : : : : : . :  :  :   :  :
TIHUBI   61"  GNGNNFVTEKECLQTCRTVAACNLPVIRGPCRAFIQLWAFDAVKGKCVLFPYGGCQGNGN 42'  NFDTEEYCMAVCGSAI
              .: . .:  . : : . . :  : :
        121"  KFYSEKECREYCGVPGDEDEELL TIBOBI: Inter-alpha-trypsin inhibitor (BPI type)
        48.1% identity in 54 aa overlap 1'                                                            EV
                                                                        : :
INSERT    1"  KADSCQLDYSQGPCLGLFKRYFYNGTSMACETFLYGGCGGNRNNFDTEEYCMAVCGSAI
TIBOBI    3"  CSEQAETGPCRAMISRWYFDVTEGKCAPFFYGGCGGNRNNFDTEEYCMAVCGSAI
              : . .   : : : : : : : .  :: ::  : : . .  : : :  :  :   :  :
         61"  CNLPIVQGPCRAFIQLWAFDAVKGKCVRFSYGGCKGNGNKFYSQKECKEYCGIPGEADER

TIBO: Basic protease inhibitor precursor-Bovine
      47.4% identity in 57 aa overlap INSERT  1'         EVCSEQAETGPCRAMISRWYFDVTEGKCAPFFYYGGCGGNRNNFD
                    : ::: :::::::: ::::::: :::::: ..:::::
TIBO    1" PSLFNRDPPIPAAQRPDFCLEPPYTGPCKARIIRYFYNAKAGLCQTFVYGGCRAKRNNFK 45' TEEYCMAVCGSAI
            .: :: .::::::
TIBO   61" SAEDCMRTCGGAIGPWGKTGGRAEGEG

FIG. 9A

```
AGTAAAGGTG ATGGCAGGAA GGCAGCCCCC GGAGGCAAAG GCTGGGCACG CGGGAGGAGA    -1134
GGCCAGAGTC AGAGGCTGCG GGTATCTCAG ATATGAAGGA AAGATGAGAG AGGCTCAGGA    -1067
AGAGGTAAGA AAAGACACAA GAGACCAGAG AAGGGAGAAG AATTAGAGAG GGAGGCAGAG    -1007
GACCGCTGTC TCTACAGACA TAGCTGGTAG AGACTGGGAG GAAGGGATGA ACCCTGAGCG     -947
                                             1
CATGAAGGA AGGAGGTGGC TGGTGGTATA TGGAGGATGT AGCTGGGGCC AGGGAAAAGA     -887
TCCTGCACTG GGGATCTGAA GCTGGGGAGA ACAGGACACG GGGTGGAGAG GCGAAAGGAG    -827
           1
GGCAGAGTGA AGCAGAGAGA CTGAGGCCTG GGGATGTGGG CATTCCGGTA GGGCACACAG    -767
                              2
TTCACTTGTC TTCTCTTTTT CCAGGAGGCC AAAGATGCTG ACGTCAAGAA CTCATAATAC    -707
CCCAGTGGGG ACCACCGCAT TCATAGCCCT GTTACAAGAA GTGGGAGATG TTCCTTTTTG    -647
TCCCAGACTG GAAATCCATT ACATCCCGAG GCTCAGGTTC TGTGGTGGTG ATCTCTGTGT    -587
GGCTTGTTCT GTGGGCCTAC CTAAAGTCCT AAGCACAGCT CTCAAGCAGA TCCGAGGCGA    -527
```

```
CTAAGATGCT AGTAGGGGTT GTCTGGAGAG AAGAGCCGAG GAGGTGGGCT GTGATGGATC   -467
AGTTCAGCTT TCAAATAAAA AGGCGTTTTT ATATTCTGTG TCGAGTTCGT GAACCCCTGT   -407
GGTGGGCTTC TCCATCTGTC TGGGTTAGTA CCTGCCACTA TACTGGAATA AGGAGACGCC   -347
TGCTTCCCTC GAGTTGGCTG GACAAGGTTA TGAGCATCCG TGTACTTATG GGGTTGCCAG   -287
CTTGGTCCTG GATCGCCCGG GCCCTTCCCC CACCCGTTCG GTTCCCCACC ACCACCCGCG   -227
                        ‾‾3‾4‾                ‾‾‾‾5‾‾‾‾           ‾4‾
CTCGTACGTG CGTCTCCGCC TGCAGCTCTT GACTCATCGG GGCCCCCGGG TCACATGCGC   -167
‾‾‾‾‾‾‾‾‾‾                                   ‾‾‾‾‾5‾‾‾‾           ‾6‾
TCGCTCGGCT CTATAGGCGC CGCCCCCCG  CCACCCCTGC CCCGGCTGG  GAGCCGCAGC   -107
‾‾‾‾‾‾‾‾‾‾‾‾‾‾‾‾‾‾‾‾‾                                                
CGCCGCCACT CCTGCTCTCT CTGCGCCGCC GCCGTCACCA CCGCCACCGC CACCGGCTGA    -47
```

FIG. 9B

APP770

Segment from APP770 (1 to 3578) to be translated:

```
         10         20         30         40         50         60         70
AGTTTCCTCG GCAGCGGTAG GCGAGAGCAC GCGGAGCAGC GTGCCGCGGG CCCCGGGAGA CGGCGGCGGT
         80         90        100        110        120        130        140
AGCGGGCGCGG GCAGAGCAAG GACGCGGGCGG ATCCCACTCG CACAGCAGCG CACTCGGTGC CCCGGCGAGG
  149          158          167          176          185          194
> ATG   CTG   CCC   GGT   TTG   GCA   CTG   CTC   CTG   GCC   GCC   TGG   ACG   GCT   CGG
  MET   Leu   Pro   Gly   Leu   Ala   Leu   Leu   Leu   Ala   Ala   Trp   Thr   Ala   Arg
  203          212          221          230          239          248
GCG   CTG   GAG   GTA   CCC   ACT   GAT   GGT   AAT   GCT   GGC   CTG   CTG   GCT   GAA   CCC   CAG   ATT
Ala   Leu   Glu   Val   Pro   Thr   Asp   Gly   Asn   Ala   Gly   Leu   Leu   Ala   Glu   Pro   Gln   Ile
  257          266          275          284          293          302
GCC   ATG   TTC   TGT   GGC   AGA   CTG   AAC   ATG   CAC   ATG   AAT   GTC   CAG   AAT   GGG   AAG   TGG
Ala   MET   Phe   Cys   Gly   Arg   Leu   Asn   MET   His   MET   Asn   Val   Gln   Asn   Gly   Lys   Trp
  311          320          329          338          347          356
GAT   TCA   GAT   CCA   TCA   GGG   ACC   AAA   ACC   TGC   ATT   GAT   ACC   AAG   GAA   GGC   ATC   CTG
Asp   Ser   Asp   Pro   Ser   Gly   Thr   Lys   Thr   Cys   Ile   Asp   Thr   Lys   Glu   Gly   Ile   Leu
```

FIG. 14A

| | | 365 | | | 374 | | | 383 | | | 392 | | | 401 | | | 410 |
|---|---|---|---|---|---|---|---|---|---|---|---|---|---|---|---|---|---|
| CAG | TAT | TGC | CAA | GAA | GTC | TAC | CCT | GAA | CTG | CAG | ATC | ACC | AAT | GTG | ACC | GTA | GAA | GCC |
| Gln | Tyr | Cys | Gln | Glu | Val | Tyr | Pro | Glu | Leu | Gln | Ile | Thr | Asn | Val | Thr | Val | Glu | Ala |
| | | 419 | | | 428 | | | 437 | | | 446 | | | 455 | | | 464 |
| AAC | CAA | GTG | ACC | ATC | CAG | AAC | CAG | GTG | ATT | CCC | TTT | CGG | GGC | AAG | CAG | TGC | AAG |
| Asn | Gln | Pro | Val | Thr | Ile | Gln | Asn | Trp | Cys | Lys | Pro | Arg | Gly | Arg | Lys | Gln | Cys | Lys |
| | | 473 | | | 482 | | | 491 | | | 500 | | | 509 | | | 518 |
| ACC | CAT | CCC | TTT | GTG | ATT | CCC | TAC | CGC | TGC | TTA | GTT | GGT | GAG | TTT | GTA | AGT |
| Thr | His | Pro | His | Phe | Val | Ile | Pro | Tyr | Arg | Cys | Leu | Val | Gly | Glu | Phe | Val | Ser |
| | | 527 | | | 536 | | | 545 | | | 554 | | | 563 | | | 572 |
| GAT | GCC | CTT | CTC | GTT | CCT | GAC | AAG | TGC | AAA | TTC | TTA | CAC | CAG | GAG | AGG | ATG | GAT |
| Asp | Ala | Leu | Leu | Val | Pro | Asp | Lys | Cys | Lys | Phe | Leu | His | Gln | Glu | Arg | MET | Asp |
| | | 581 | | | 590 | | | 599 | | | 608 | | | 617 | | | 626 |
| GTT | TGC | GAA | ACT | CAT | CTT | CAC | TGG | ATG | GTC | ACC | GCC | AAA | GAG | ACA | TGC | AGT | GAG |
| Val | Cys | Glu | Thr | His | Leu | His | Trp | MET | Val | Thr | Ala | Lys | Glu | Thr | Cys | Ser | Glu |
| | | 635 | | | 644 | | | 653 | | | 662 | | | 671 | | | 680 |
| AAG | AGT | ACC | AAC | TTG | CAT | GAC | TAC | GGC | ATG | TTG | CTG | CCC | TGC | GGA | ATT | GAC | AAG |
| Lys | Ser | Thr | Asn | Leu | His | Asp | Tyr | Gly | MET | Leu | Leu | Pro | Cys | Gly | Ile | Asp | Lys |
| | | 689 | | | 698 | | | 707 | | | 716 | | | 725 | | | 734 |
| TTC | CGA | GGG | GTA | GAG | TTT | GTG | TGT | CCA | CTG | GCT | GAA | GAA | AGT | GAC | AAT | GTG |
| Phe | Arg | Gly | Val | Glu | Phe | Val | Cys | Pro | Leu | Ala | Glu | Glu | Ser | Asp | Asn | Val |

FIG. 14B

| | 743 | 752 | 761 | 770 | 779 | 788 |
|---|---|---|---|---|---|---|
| GAT | GCT | GAT | GCG | GAG | GAT | GAC |
| Asp | Ser | Asp | Ala | Glu | Asp | Asp |
| | 797 | 806 | 815 | 824 | 833 | 842 |
| ACA | GAC | TAT | GCA | GAT | TCG | GAT | GTC | TGG | TGG | GGA | GCA | GAC |
| Thr | Asp | Tyr | Ala | Asp | Ser | Asp | Val | Trp | Trp | Gly | Ala | Asp |
| | 851 | 860 | 869 | 878 | 887 | 896 |
| ACA | GAC | TAT | GCA | AGT | GAA | GAC | AAA | GTA | GTA | GCA | GAG | GAA |
| Thr | Asp | Tyr | Ala | Ser | Glu | Asp | Lys | Val | Val | Ala | Glu | Glu |
| | 905 | 914 | 923 | 932 | 941 | 950 |
| GAA | GCT | GAG | GTG | GAA | GAA | GAA | GCC | GAT | GAC | GAG | GAC | GAT |
| Glu | Ala | Glu | Val | Glu | Glu | Glu | Ala | Asp | Asp | Glu | Asp | Asp |
| | 959 | 968 | 977 | 986 | 995 | 1004 |
| GGT | GAT | GTA | GCT | GAA | GAG | CCC | TAC | GAA | GCC | ACA | GAG | AGA |
| Gly | Asp | Val | Ala | Glu | Glu | Pro | Tyr | Glu | Ala | Thr | Glu | Arg |
| | 1013 | 1022 | 1031 | 1040 | 1049 | 1058 |
| ACC | AGC | ATT | GCC | ACC | ACC | ACC | ACA | ACC | GAG | TCT | GAA | GAG | GTG |
| Thr | Ser | Ile | Ala | Thr | Thr | Thr | Thr | Thr | Glu | Ser | Glu | Glu | Val |
| | 1067 | 1076 | 1085 | 1094 | 1103 | 1112 |
| GTT | CGA | GAG | GTG | TCT | TGC | GCC | CAA | GAG | ACG | GAG | GCC | CCG | TGC | CGA | GCA | ATG | ATC |
| Val | Arg | Glu | Val | Ser | Cys | Ala | Gln | Glu | Thr | Glu | Ala | Pro | Cys | Arg | Ala | MET | Ile |
| TCC | CGC | TGG | TAC | TTT | GAT | GTG | ACT | GAA | GGG | AAG | TGT | GCC | CCA | TTC | TTT | TAC | GGC |
| Ser | Arg | Trp | Tyr | Phe | Asp | Val | Thr | Glu | Gly | Lys | Cys | Ala | Pro | Phe | Phe | Tyr | Gly |

```
     1121      1130      1139      1148      1157      1166
GGA  TGT  GGC  AAC  CGG  AAC  TTT  GAC  ACA  GAA  GAG  TAC  TGC  ATG  GCC  GTG
Gly  Cys  Gly  Asn  Arg  Asn  Phe  Asp  Thr  Glu  Glu  Tyr  Cys  MET  Ala  Val 1175                1184                1193                1211      1220
TGT  GGC  AGC  GCC  ATG  TCC  CAA  AGT  TTA  CTC  AAG  ACT  ACC  CAG  GAA  CCT  CTT  GCC
Cys  Gly  Ser  Ala  MET  Ser  Gln  Ser  Leu  Leu  Lys  Thr  Thr  Gln  Glu  Pro  Leu  Ala 1229                1238                1247                1256      1265      1274
CGA  GAT  GTT  CCT  AAA  CTT  CCT  ACA  ACA  GCA  GCC  AGT  ACC  CCT  GAT  GCC  GTT  GAC
Arg  Asp  Val  Pro  Lys  Leu  Pro  Thr  Thr  Ala  Ala  Ser  Thr  Pro  Asp  Ala  Val  Asp 1283                1292                1301                1310      1319      1328
AAG  TAT  CTC  GAG  ACA  CCT  GGG  GAT  GAG  AAT  GAA  CAT  GCC  CAT  TTC  CAG  AAA  GCC
Lys  Tyr  Leu  Glu  Thr  Pro  Gly  Asp  Glu  Asn  Glu  His  Ala  His  Phe  Gln  Lys  Ala 1337                1346                1355                1364      1373      1382
AAA  GAG  AGG  CTT  GAG  GCC  AAG  CAC  CGA  GAG  AGA  ATG  TCC  CAG  GTC  ATG  AGA  GAA
Lys  Glu  Arg  Leu  Glu  Ala  Lys  His  Arg  Glu  Arg  MET  Ser  Gln  Val  MET  Arg  Glu 1391                1400                1409                1418      1427      1436
TGG  GAA  GCA  GAA  CGT  CAA  GCA  AAG  AAC  TTG  CCT  AAA  GCT  GAT  AAG  AAG  GCA
Trp  Glu  Ala  Glu  Arg  Gln  Ala  Lys  Asn  Leu  Pro  Lys  Ala  Asp  Lys  Lys  Ala 1445                1454                1463                1472      1481      1490
GTT  ATC  CAG  CAT  TTC  CAG  GAG  AAA  GTG  GAA  TCT  TTG  GAA  CAG  GAA  GCA  GCC  AAC
Val  Ile  Gln  His  Phe  Gln  Glu  Lys  Val  Glu  Ser  Leu  Glu  Gln  Glu  Ala  Ala  Asn
```

|  | 1499 | 1508 | 1517 | 1526 | 1535 | 1544 |
|---|---|---|---|---|---|---|
| GAG | AGA | CAG | CTG | GTG | GAG | ACA | CAC | ATG | GCC | AGA | GTG | GAA | GCC | ATG | CTC | AAT |
| Glu | Arg | Gln | Leu | Val | Glu | Thr | His | MET | Ala | Arg | Val | Glu | Ala | MET | Leu | Asn |

|  | 1553 | 1562 | 1571 | 1580 | 1589 | 1598 |
|---|---|---|---|---|---|---|
| GAC | CGC | CGC | CTG | GCC | GAG | AAC | TAC | ATC | ACC | GCT | CTG | CAG | GCT | GTT | CCT |
| Asp | Arg | Arg | Leu | Ala | Glu | Asn | Tyr | Ile | Thr | Ala | Leu | Gln | Ala | Val | Pro |

|  | 1607 | 1616 | 1625 | 1634 | 1643 | 1652 |
|---|---|---|---|---|---|---|
| CCT | CGG | CCT | CAC | CGT | GTG | TTC | AAT | ATG | CTA | AAG | AAG | TAT | CGC | GCA | GAA | CAG |
| Pro | Arg | Pro | His | Arg | Val | Phe | Asn | MET | Leu | Lys | Lys | Tyr | Arg | Ala | Glu | Gln |

|  | 1661 | 1670 | 1679 | 1688 | 1697 | 1706 |
|---|---|---|---|---|---|---|
| AAG | GAC | AGA | CAG | CAC | ACC | CTA | AAG | CAT | TTC | GAG | GTT | ATG | GTC | TAT | GTG | CCC |
| Lys | Asp | Arg | Gln | His | Thr | Leu | Lys | His | Phe | Glu | Val | MET | Val | Tyr | Val | Pro |

|  | 1715 | 1724 | 1733 | 1742 | 1751 | 1760 |
|---|---|---|---|---|---|---|
| AAG | AAA | GCC | GCT | CAG | ATC | CGG | TCC | CAG | GTT | ATG | ACA | CAC | CTC | ATG | GTG | GAT |
| Lys | Lys | Ala | Ala | Gln | Ile | Arg | Ser | Gln | Val | MET | Thr | His | Leu | MET | Val | Asp |

|  | 1769 | 1778 | 1787 | 1796 | 1805 | 1814 |
|---|---|---|---|---|---|---|
| AAG | CGC | ATG | AAT | CAG | TCT | CTC | TCC | TAC | AAC | GTG | CCT | GCA | GTG | ATT | TAT |
| Lys | Arg | MET | Asn | Gln | Ser | Leu | Ser | Tyr | Asn | Val | Pro | Ala | Val | Ile | Tyr |

|  | 1823 | 1832 | 1841 | 1850 | 1859 | 1868 |
|---|---|---|---|---|---|---|
| GAG | CGC | ATG | AAT | CAG | GTT | GAT | GAG | CTG | CTT | CAG | GAG | AAA | CAA | AAC | GCC | GAG |
| Glu | Arg | MET | Asn | Gln | Val | Asp | Glu | Leu | Leu | Gln | Glu | Lys | Gln | Asn | Ala | Glu |

|  |
|---|
| GAG | ATT | CAG | GAT | GAA | GTT | GAT | GAG | CTG | CTC | CAG | GAG | AAA | CAA | AAC | TAT | TCA | GAT |
| Glu | Ile | Gln | Asp | Glu | Val | Asp | Glu | Leu | Leu | Gln | Glu | Lys | Gln | Asn | Tyr | Ser | Asp |

FIG. 14E

|  | 1877 | 1886 | 1895 | 1904 | 1913 | 1922 |
|---|---|---|---|---|---|---|
| GAC | GTC | GCC | AAC | ATG | ATT | AGT | GAA | CCA | AGG | ATC | AGT | TAC | GGA | AAC | GAT | GCT |
| Asp | Val | Ala | Asn | MET | Ile | Ser | Glu | Pro | Arg | Ile | Ser | Tyr | Gly | Asn | Asp | Ala |

|  | 1931 | 1940 | 1949 | 1958 | 1967 | 1976 |
|---|---|---|---|---|---|---|
| CTC | ATG | CCA | TCT | TTG | ACC | GAA | ACG | AAA | ACC | ACC | GTG | GAG | CTC | CTT | CCC | GTG | AAT |
| Leu | MET | Pro | Ser | Leu | Thr | Glu | Thr | Lys | Thr | Thr | Val | Glu | Leu | Leu | Pro | Val | Asn |

|  | 1985 | 1994 | 2003 | 2012 | 2021 | 2030 |
|---|---|---|---|---|---|---|
| GGA | GAG | TTC | AGC | GAC | GAT | CTC | CAG | CCG | TGG | CAT | TCT | GGG | TTT | GCT | GAC | TCT |
| Gly | Glu | Phe | Ser | Leu | Asp | Asp | Leu | Gln | Pro | Trp | His | Ser | Phe | Ala | Asp | Ser |

|  | 2039 | 2048 | 2057 | 2066 | 2075 | 2084 |
|---|---|---|---|---|---|---|
| GTG | CCA | GCC | AAC | ACA | GAA | AAC | GAA | GTT | GAG | CCT | GTT | GAT | GCC | CGC | CCT | GCT | GCC |
| Val | Pro | Ala | Asn | Thr | Glu | Asn | Glu | Val | Glu | Pro | Val | Asp | Ala | Arg | Pro | Ala | Ala |

|  | 2093 | 2102 | 2111 | 2120 | 2129 | 2138 |
|---|---|---|---|---|---|---|
| GAC | CGA | GGA | CTG | ACC | ACT | CGA | CCA | GGT | TCT | TGG | TTG | ACA | AAT | ATC | AAG | ACG | GAG |
| Asp | Arg | Gly | Leu | Thr | Thr | Arg | Pro | Gly | Ser | Gly | Leu | Thr | Asn | Ile | Lys | Thr | Glu |

|  | 2147 | 2156 | 2165 | 2174 | 2183 | 2192 |
|---|---|---|---|---|---|---|
| GAG | TCT | GAA | GTG | AAG | ATG | GAT | GCA | GAA | TTC | CGA | CAT | GAC | TCA | GGA | TAT | GAA |
| Glu | Ser | Glu | Val | Lys | MET | Asp | Ala | Glu | Phe | Arg | His | Asp | Ser | Gly | Tyr | Glu |

|  | 2201 | 2210 | 2219 | 2228 | 2237 | 2246 |
|---|---|---|---|---|---|---|
| GTT | CAT | CAA | AAA | TTG | GTG | TTC | TTT | GCA | GAA | GAT | GTG | GGT | TCA | AAC | AAA | GGT |
| Val | His | Gln | Lys | Leu | Val | Phe | Phe | Ala | Glu | Asp | Val | Gly | Ser | Asn | Lys | Gly |

FIG. 14F

```
      2255           2264           2273           2282           2291           2300
GCA ATC ATT GGA CTC ATG GTG GGC GGT GTT GTC ATA GCG ACA GTG ATC GTC ATC
Ala Ile Ile Gly Leu MET Val Gly Gly Val Val Ile Ala Thr Val Ile Val Ile
      2309           2318           2327           2336           2345           2354
ACC TTG GTG ATG CTG AAG AAA CAG TAC ACA TCC ATT CAT CAT GGT GTG GTG
Thr Leu Val MET Leu Lys Lys Gln Tyr Thr Ser Ile His His Gly Val Val
      2363           2372           2381           2390           2399           2408
GAG GTT GAC GCC GCT ACC GTC CCA GAG GAG CGC CAC CTG TCC AAG ATG CAG CAG
Glu Val Asp Ala Ala Thr Val Pro Glu Glu Arg His Leu Ser Lys MET Gln Gln
      2417           2426           2435           2444           2453
AAC GGC TAC GAA AAT CCA ACC TAC AAG TTC TTT GAG CAG ATG CAG AAC TAG A
Asn Gly Tyr Glu Asn Pro Thr Tyr Lys Phe Phe Glu Gln MET Gln Asn 2470           2480           2490           2500           2510           2520           2530
CCCCCGCCAC AGCAGCCTCT GAAGTTGGAC AGCAAAACCA TTGCTTCACT ACCCATCGGT GTCCATTTAT 2540           2550           2560           2570           2580           2590           2600
AGAATAATGT GGGAAGAAAC AAACCCGTTT TATGATTTAC TCATTATCGC CTTTTGACAG CTGTGCTGTA 2610           2620           2630           2640           2650           2660           2670
ACACAAGTAG ATGCCTGAAC TTGAATTAAT CCACACATCA GTAATGTATT CTATCTCTCT TTACATTTTG
```

FIG. 14G

```
           2680        2690        2700        2710        2720        2730        2740
GTCTCTATAC TACATTATTA ATGGGTTTTG TGTACTGTAA AGAATTAGC TGTATCAAAC TAGTGCATGA 2750        2760        2770        2780        2790        2800        2810
ATAGATTCTC TCCTGATTAT TTATCACATA GCCCCCTAGC CAGTGTATA TTATTCTTGT GGTTTGTGAC 2820        2830        2840        2850        2860        2870        2880
CCAATTAAGT CCTACTTTAC ATATGCTTTA AGAATCGATG GGGGATGCTT CATGTGAACG TGGGAGTTCA 2890        2900        2910        2920        2930        2940        2950
GCTGCTTCTC TTGCCTAAGT ATTCCTTTCC TGATCACTAT GCATTTAAA GTTAAACATT TTTAAGTATT 2960        2970        2980        2990        3000        3010        3020
TCAGATGCTT TAGAGAGATT TTTTTTCCAT GACTGCATTT TACTGTACAG ATTGCTGCTT CTGCTATATT 3030        3040        3050        3060        3070        3080        3090
TGTGATATAG GAATTAAGAG GATACACACG TTTGTTTCTT CGTGCCTGTT TTATGTGCAC ACATTAGGCA 3100        3110        3120        3130        3140        3150        3160
TTGAGACTTC AAGCTTTTCT TTTTTGTCC ACGTATCTTT GGGTCTTTGA TAAAGAAAAG AATCCCTGTT
```

```
     3170       3180       3190       3200       3210       3220       3230
CATTGTAAGC ACTTTTACGG GGCGGGTGGG GAGGGGTGCT CTGCTGGTCT TCAATTACCA AGAATTCTCC 3240       3250       3260       3270       3280       3290       3300
AAAACAATTT TCTGCAGGAT GATTGTACAG AATCATTGCT TATGACATGA TCGCTTTCTA CACTGTATTA 3310       3320       3330       3340       3350       3360       3370
CATAAATAAA TTAAATAAAA TAACCCCGGG CAAGACTTTT CTTTGAAGGA TGACTACAGA CATTAAATAA 3380       3390       3400       3410       3420       3430       3440
TCGAAGTAAT TTTGGGTGGG GAGAAGAGGC AGATTCAATT TTCTTTAACC AGTCTGAAGT TTCATTTATG 3450       3460       3470       3480       3490       3500       3510
ATACAAAAGA AGATGAAAAT GGAAGTGGCA ATATAAGGGG ATGAGGAAGG CATGCCTGGA CAAACCCTTC 3520       3530       3540       3550       3560       3570
TTTTAAGATG TGTCTTCAAT TTGTATAAAA TGGTGTTTTC ATGTAAATAA ATACATTCTT GGAGGAGC
```

TRANSGENIC MICE DISPLAYING THE AMYLOID-FORMING PATHOLOGY OF ALZHEIMER'S DISEASE

CROSS-REFERENCE

This application is a continuation-in-part of my earlier filed pending U.S. application Ser. No. 07/538,857, filed Jun. 15, 1990, now abandoned, which application is incorporated herein by reference in its entirety and to which application I claim priority under 35 U.S.C. §120.

TABLE OF CONTENTS

Cross-Reference
1. Field of the Invention
2. Background of the Invention
   2.1. Genetic Transformations
   2.2. Alzheimer's Disease and β-Amyloid Protein
3. Summary of the Invention
   3.1. Objects, Features and Advantages
4. Brief Description of the Drawings
5. Detailed Description of the Preferred Embodiments
   5.1. Definitions
   5.2. Disclosure Overview and Organization
   5.3. DNA Sequences
   5.4. Protein Production
   5.5. Promoter/A4 Sequence Fusion Constructs
   5.6. Transgenic Organisms
   5.7. Methods and Materials
      5.7.a. Hosts and Controls Sequences
      5.7.b. Transformations
      5.7.c. Vector Construction
      5.7.d. Verification of Construction
6. EXAMPLES
   6.1. EXAMPLE 1: Expression of β-Amyloid-Related Protein (1–751) in Cultured Mammalian Cells
   6.2. EXAMPLE 2: Expression of β-Amyloid Precursor in Mammalian Cells
   6.3. EXAMPLE 3: Assay to Distinguish Genetic Variants of β-Amyloid-Related Protein mRNA Species
   6.4. EXAMPLE 4: Construction of the NSE-A42 and A99 Transgenic Expression Plasmids
   6.5. EXAMPLE 5: Construction of the NSE-A695 and the NSE-A751 Transgenic Expression Plasmids
   6.6. EXAMPLE 6: Preparation of the Metallothionein A42 and Metallothionein A99 Transgenic Expression Plasmids
   6.7. EXAMPLE 7: Construction of MT-A751 and MT-A695 Transgenic Expression Plasmids
   6.8. EXAMPLE 8: Collecting and Injecting the Eggs
      6.8.a. Procedure
      Table 1
      EXAMPLE 9: Determination of Transgene Copy Numbers
      6.8.b. Analysis
      EXAMPLE 10: RNA Expression of Inherited Transgenes
      EXAMPLE 11: Western Blot Analysis
      EXAMPLE 12: Histological Analysis of Transgenic Mouse Brains with Monoclonal Antibody 4.1
      Table 2
7. Uses of the Invention
8. Deposits
9. Claims
10. Abstract of the Disclosure
11. Figures

1. Field of the Invention

The invention relates generally to animal models useful in testing a hypothesis related to the treatment of a disease. More specifically, it relates to transgenic mammals which have had incorporated in their genome specific segments of exogenous genetic material which encode for and in specific cell types will ubiquitously over-express β-amyloid proteins, their precursors and portions of such proteins and precursors.

2. Background of the Invention

The background of the present invention is twofold in that it relates to: (1) biological organisms which have been genetically transformed; and (2) a study of genetic material related to amyloidosis. Both of these areas are discussed below.

2.1. Genetic Transformations.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases.

The genetic transformation of a zygote (and the organisms which matures therefrom) is carried out by the addition of exogenous genetic material in a manner such that the exogenous genetic material becomes part of the nucleic portion of the zygote prior to a division of the zygote. If the exogenous genetic material is added after mitosis or cell division of the zygote, the exogenous genetic material must be added to each resulting nucleus. However, there is a possibility that the exogenous genetic material may not be integrated into and become a part of the genetic material of the zygote and the organism which results therefrom. Thus, the exogenous genetic material can be added to any nucleic genetic material which ultimately forms a part of the nucleus of the zygote, including the zygote nucleus.

The nucleic genetic material of the organism being transformed must be in a physical state which enables it to take up the exogenous genetic material. There are numerous ways of accomplishing this. For example, the exogenous genetic material can be placed in the nucleus of a primordial germ cell which is diploid, e.g., a spermatogonium or oogonium. The primordial germ cell is then allowed to mature to a gamete, which is then united with another gamete or source of a haploid set of chromosomes to form a zygote.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

Attempts have been made to study a number of different types of genetic diseases utilizing such transgenic animals. Attempts related to studying Alzheimer's disease are disclosed within published PCT application WO89/06689 and PCT application WO89/06693, both published on Jul. 27, 1989, which published applications are incorporated herein by reference to disclose genetic sequences coding for Alzheimer's β-amyloid protein and the incorporation of such sequences into the genome of transgenic animals.

As described in detail below, the production of β-amyloid protein is believed to be related to Alzheimer's disease. However, a serious obstacle to elucidating the molecular mechanism involved in amyloid synthesis and deposition in an Alzheimer's diseased brain has been the unavailability of convincing animal models for this uniquely human disorder. Published PCT applications WO89/06689 and WO89/06693 disclose particular DNA sequences believed to be related to the production of amyloid. These particular sequences are fused to newly developed tumor virus vectors, derived from Sumian Virus 40 (SV 40) and the JC virus to produce constructs. These constructs are utilized to transfect cells and transgenic mice to establish models for amyloid overexpression, which may be related to amyloid accumulation in the Alzheimer's-diseased brain.

The transgenic animals produced in accordance with the present invention are intended to provide an experimental medium for elucidating aspects of the molecular pathogenesis of Alzheimer's disease and to serve as tools for screening drugs that may have potential application as therapeutic agents to prevent or limit amyloid accumulation.

2.2. Alzheimer's Disease and β-Amyloid Protein

It is estimated that over 5% of the U.S. population over 65 and over 15% of the U.S. population over 85 are beset with some form of Alzheimer's disease (Cross, A. J., *Eur J Pharmacol* (1982) 82:77–80; Terry, R. D., et al., *Ann Neurol* (1983) 14:497506). It is believed that the principal cause for confinement of the elderly in long term care facilities is due to this disease, and approximately 65% of those dying in skilled nursing facilities suffer from it.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most prevalent (Price, D. L., et al., *Drug Development Research* (1985) 5:59–68). Plaques are also seen in the brains of aged Down's Syndrome patients who develop Alzheimer's disease.

The protein which makes up the bulk of these plaques has been partially purified and sequenced. Plaque-rich brains of deceased Alzheimer's patients have been used as a source to extract an approximately 4.2 kd "core" polypeptide, amyloid plaque-core protein (APCP), herein referred to as "β-amyloid core protein." This peptide was designated β-protein by Glenner, G., et al., [*Biochem Biophys Res Commun* (1984) 120:885–890]. The amino acid sequence of the amino-terminus has been determined [Glenner, G., et al., *Biochem Biophys Res Commun* (1984) 122:1131–1135; Masters, C. L., et al., *Proc Natl Acad Sci USA* (1985) 82:4245–4259] and the amino acid sequences reported by the two groups are identical except that Glenner et al., report a glutamine at position 11 for Alzheimer Disease cerebral vascular amyloid whereas Masters et al., report glutamic acid at position 11. Also, the former authors report that the cerebral vascular amyloid has a unique amino-terminus while the latter authors report that the form found in amyloid plaque cores has a "ragged" amino-terminus—i.e., peptides isolated from this source appear to be missing 3, 7, or 8 amino acids from the amino-terminus. Both groups have shown that the same peptide is found in the amyloid plaque cores and vascular amyloid of adult Down's syndrome-afflicted individuals and report glutamic acid at position 11.

Further studies on the β-amyloid core protein were also conducted by Roher, A., et al., *Proc Natl Acad Sci USA* (1986) 83:2662–2666 which showed the complete amino acid composition of the β-protein, and verified that it matched that of no known protein. The compositions obtained were, however, evidently not in agreement with those of Allsop, D., et al., *Brain Res* (1983) 259:348352; nor were they in agreement with those published by Glenner or Masters (supra).

Wong, C. W., et al., *Proc Natl Acad Sci USA* (1985) 82:8729–8732 showed that a synthetic peptide which was homologous to the first ten amino acids of the β-amyloid core protein described by Masters (supra) was able to raise antibodies in mice and that these antibodies could be used to stain not only amyloid-laden cerebral vessels, but neuritic plaques as well. These results were confirmed by Allsop, D. et al., *Neuroscience Letters* (1986) 68:252–256 using monoclonal antibodies directed against a synthetic peptide corresponding to amino acids 8–17. Thus, in general, the plaque protein found in various locations of the brain of Alzheimer's patients appears to be similar in immunoreactivity. It is highly insoluble, as shown by the inability to achieve solubilization in many commonly used denaturants such as detergents and chaotropic agents (Masters, supra, Allsop, D., et al., (supra)).

It is believed, by analogy to some other amyloid proteins, that β-amyloid core protein may be formed from a precursor in the peripheral circulatory system or lymphatic system. There are six known instances of disease-associated amyloid deposits in which the nature of the precursor protein for the amyloid protein is known: for primary amyloidosis, the source is an immunoglobulin light chain; for secondary amyloidosis, the precursor is amyloid A protein; for familial amyloid polyneuropathy and senile cardiac amyloidosis, prealbumin also known as transthyreitin or a variant thereof; for medullary carcinoma of thyroid, a procalcitonin fragment; and for hereditary cerebral hemorrhage, gamma-trace fragment which has been shown to be cystatin C. (See, e.g., Glenner, G. *New England Journal of Medicine* (1980) 302:1283; Sletton, K., et al., *Biochem J* (1981) 195:561; Benditt, et al., *FEBS Lett* (1971) 19:169; Sletton, K., et al., *Eur J Biochem* (1974) 41:117; Sletton, K., et al., *J Exp Med* (1976) 143:993). The foregoing is a partial list and there are at least a number of additional references with regard to procalcitonin fragment as a precursor for the amyloid of the thyroid carcinoma. Alternatively, or additionally, such a precursor for β-amyloid core protein may be produced in the brain or elsewhere and is specifically deposited in the brain.

It has been described that a protein containing the β-amyloid core protein (referred to as A4) sequence within the framework of a larger protein exists (Kang, J., et al., *Nature* (1987) 325:733-736). This protein, which is a potential precursor in vivo to the β-amyloid core protein, was predicted from the sequence of a cDNA clone isolated from a human fetal brain tissue cDNA library and consists of 695 amino acid residues (referred to as A695) wherein the amino terminus of the β-amyloid core protein begins at position 597. By analogy to the above described series, it may be that such a precursor or a fragment thereof circulates in the serum at a higher level differentiable in Alzheimer's victims relative to unafflicted individuals. Alternatively or additionally, such differences may be detected in the cerebral spinal fluid.

It appears as though there are a number of precursor proteins in addition to A695, which was described by Kang et al. One such precursor protein is described in copending U.S. application Ser. No. 361,912, filed Jun. 6, 1989, by researchers from the same research organization as the present inventors (A751). Others have characterized an additional amyloid precursor protein (see Kitaguchi et al., *Nature* 331:530–532 (1988), which is slightly larger, 770 amino acids. It is pointed out that these A751 and A770 proteins contain an approximately 57 amino acid insert beyond A695. This particular 57 amino acid insert sequence is highly homologous to a number of Kunitz-type inhibitors which are specific for a number of serine proteases. An additional 19 amino acids are present adjacent to the 57 amino acid insert in the A770 form.

As indicated by the above publications and numerous other publications not cited, the genetic material encoding for the production of β-amyloid precursor proteins are the subject of intensive study. However, at present, there is no direct verifiable information available on the specific mechanisms that regulate the production and deposit of amyloid protein in an Alzheimer's diseased brain. It is known that the genetic material encoding for the production of β-amyloid precursor protein is on chromosome 21. Further, numerous studies suggest that there are complex interactions involving the genetic material on this chromosome. Such interactions are believed to involve the production of precursor proteins, proteases and protease inhibitors. Further, it is believed that in individuals suffering from Alzheimer's disease these interactions are somehow skewed so that an unusually high content of β-amyloid core protein is produced and/or deposited in the brain. The high β-amyloid core protein concentration could be the result of a variety of biochemical activities including the overproduction of such proteins and/or the inability to cleave sufficient numbers of such proteins once cleaved.

The transgenic mammals of the present invention will provide insights with respect to how and where these interactions occur and thus provide more useful models for testing the efficacy of certain drugs in preventing or reducing the accumulation of β-amyloid core protein in the brain. The transgenic non-human mammals of the present invention include recombinant genetic material comprised of specific segments of β-amyloid precursor proteins which segments are fused to specific promoters capable of expressing the protein in specific tissues such as nerve tissues generally and/or specific types of nerve tissue, e.g., the brain.

3. Summary of the Invention

The invention provides a means for elucidating the molecular mechanisms involved in the synthesis of and, more importantly, inhibiting the synthesis and deposition of β-amyloid protein (most importantly, in the brain) by inhibiting production and/or increasing cleavage after production. Cloned recombinant or synthetic DNA sequences related to the pathology of Alzheimer's disease are injected into fertilized mammalian eggs (preferably mice eggs). The injected eggs are implanted in pseudopregnant females and are grown to term to provide transgenic mice whose cells express proteins related to the pathology of Alzheimer's disease. The injected sequences are constructs having promoter sequences connected so as to express the desired protein in specific tissues of the transgenic mammals.

It is believed that β-amyloid core protein A99 and A42 (as defined herein) are first expressed in the form of precursor proteins A695 and/or A751. The precursor proteins may be subjected to the action of a protease enzyme which allows for the formation of β-amyloid core proteins, which, when produced in sufficient amounts, allows for the formation of plaques associated with Alzheimer's disease. An important aspect of the present invention relates to sequences which code for the production of any of A42, A99, A695, and A751 in specific cells (e.g., nerve cells) and to a sequence which codes for a protease inhibitor, which inhibits the action of the proteolytic enzyme which may be responsible for converting precursor β-amyloid proteins into β-amyloid core proteins or which may inhibit a proteolytic enzyme (or enzymes) directed to catabolize or degrade the β-amyloid core protein.

In connection with the present invention nucleotide sequences which encode for the production of specific β-amyloid precursor proteins and β-amyloid core proteins are linked to specific promoter sequences. The promoter sequences are carefully chosen so that some sequences express the nucleotide sequence they are attached to in all types of tissues whereas other promoter sequences only express the nucleotide they are attached to when the promoter is present within specific types of cells of a specific type of tissue e.g., nerve tissue. By producing such transgenic mice, additional information can be obtained with respect to how and where β-amyloid core proteins are produced (and sometimes degraded) and deposited in an Alzheimer's diseased brain. Using this additional information regarding the mechanism and location of the production (and possible degradation) and deposition of β-amyloid core proteins, therapeutic agents can be more effectively tested with respect to their ability to prevent the production and/or deposition of such proteins and thus alleviate or prevent Alzheimer's disease.

Further, an important aspect of this invention is the production of transgenic mammals which include DNA sequences that encode for analogs of a 57-amino acid protease inhibitor, which analogs contain at least one amino acid substitution which is effective to yield an inhibitor having altered protease specificity. The transgenic mammals of this invention provide useful models for studying the in vivo relationships of the proteins to each other and to other compounds being tested for their usefulness in treating Alzheimer's disease.

3.1 Objects, Features and Advantages

A primary object of this invention is to provide a transgenic non-human mammal whose cells include a recombinant DNA sequence coding for cell type specific expression of β-amyloid proteins or analogs thereof, which mammals can be used for the study of the etiology of Alzheimer's disease and the efficacy of drugs in treating the disease.

An advantage of the present invention is that it provides an in vivo means for studying the effects of expressing different proteins in different tissues (e.g., nerve tissue including specific types of nerve tissues and non-nerve tissue) vis-a-vis the synthesis of β-amyloid protein and the formation of plaques associated with Alzheimer's disease.

Another object of the invention is to provide a transgenic non-human mammal whose cells include a recombinant DNA sequence comprising a cell specific promoter sequence and a sequence coding for one or more β-amyloid precursor proteins alone or with certain protease inhibitor proteins which can be used for the study of the etiology of Alzheimer's disease.

Yet another object of the invention is to provide transgenic mice which have in their cells unique promoter/coding sequences which ubiquitously express β-amyloid precursor protein in nerve tissue and nerve tissue subtypes and/or all types of tissue.

A further aspect of the invention relates to synthesis and use of promoter/coding constructs which express the β-amyloid precursor proteins alone or in combination with inhibitor proteins in various tissues of transgenic mammals incorporating such constructs in their genome. A feature of the transgenic mammals of the invention is that they provide both prognostic and diagnostic means for the study of Alzheimer's disease and for determining the efficacy of pharmaceutical drugs in treating Alzheimer's disease in a test subject. Initially, the transgenic mice are used as standards to identify one or more candidate compounds capable of metabolizing the β-amyloid protein (or preventing its formation) which is associated with a predisposition to Alzheimer's disease.

Yet another aspect of the invention relates to a transgenic mammal incorporated with recombinant DNA sequences comprised of tissue specific promoter sequences and sequences coding for the expression of a 57 amino acid protease inhibitor and/or analogs thereof including a promoter specifically capable of expressing the inhibitor in nerve tissue.

Other objects, advantages and features of the present invention include providing transgenic non-human mammals which provide information regarding the mechanism and location of β-amyloid core protein production and disposition as well as providing in vivo models for testing drugs capable of interfering with or preventing such production and/or disposition.

These and other objects, features and advantages of the invention will become more fully apparent when the following detailed description of the invention is read in conjunction with the accompanying figures.

4. Brief Description of the Drawings

FIG. 1(A–H) shows the base sequence of a cDNA clone, designated λAPCP168i4, which encodes amino acids 1–751 of β-amyloid precursor protein. The 168 bp insert, which distinguishes this clone from the Kang et al. sequence, is underlined.

FIG. 2 shows the amino acid sequence of A99.

FIG. 3 shows the amino acid sequence of A42 corresponding to the β-amyloid core protein.

FIG. 8(A–B) shows the relatedness of the peptide encoded by the λAPCP168i4 168 bp insert to a superfamily of proteins many of whose members exhibit inhibitory activity for serine proteases.

FIG. 14(A–I) shows the nucleotide sequence and amino acids of the β-amyloid precursor protein A770 (see Kitaguchi et al. in *Nature*, volume 331, Feb. 11, 1988)

5. Detailed Description of Preferred Embodiments

Figure 4A:
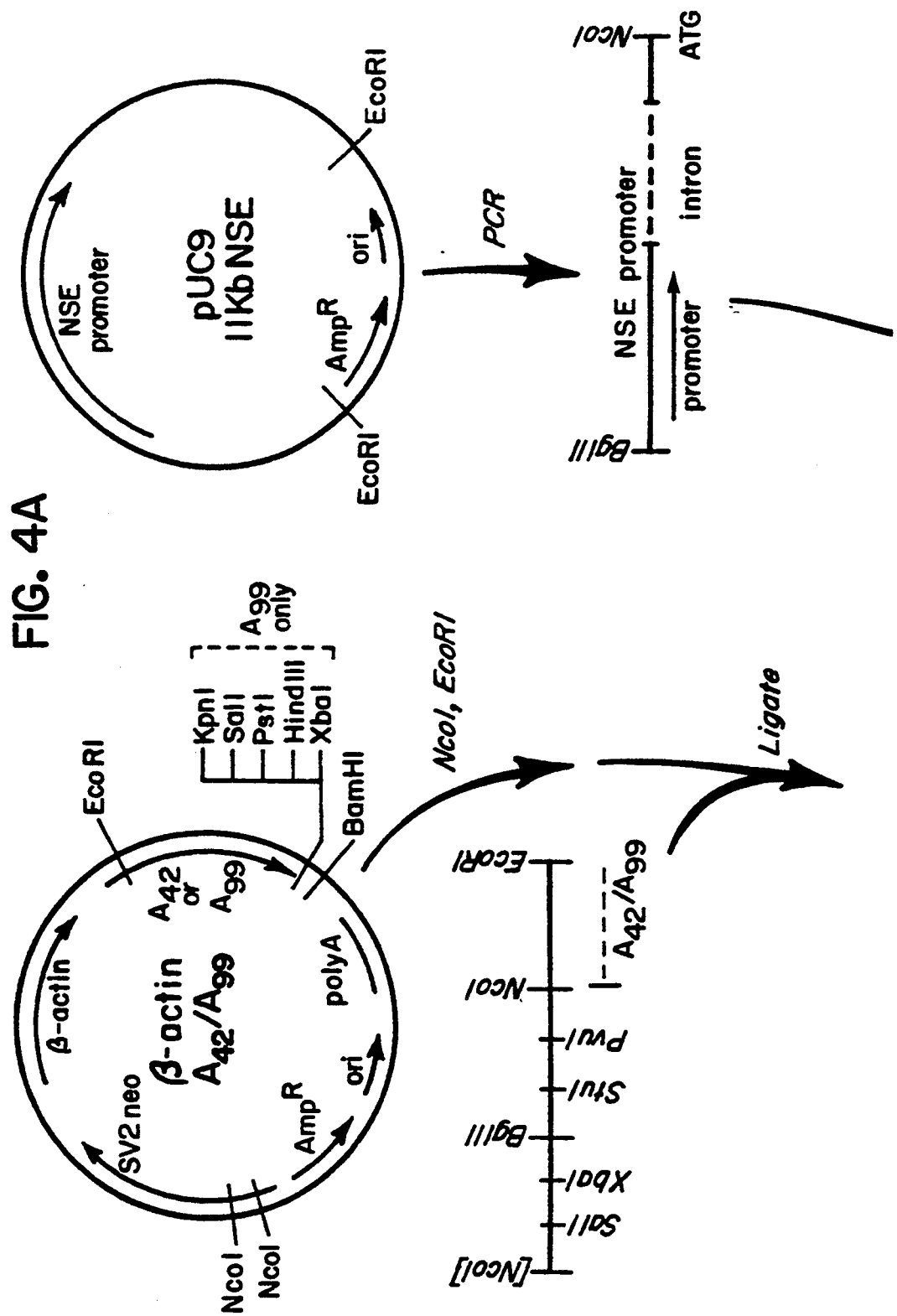
FIG. 4(A–B) shows the construction strategy for the NSE promoter linked to A42 and to A99.

Before the present transgenic mice and process for making and using such to test drugs are described, it is to be understood that this invention is not limited to the particular processes and materials described as such methods and materials may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a" "an" and "the" include plural referents unless the context clearly dictates otherwise. Thus, for example, reference to "a clone" or "a sequence" includes mixtures of clones or sequences of the type described, reference to "an amyloid protein" includes reference to mixtures of such proteins of the type described, and reference to "the transgenic mouse" includes different species of such mice and so forth.

5.1. Definitions

The terms "core protein" and $\beta$-amyloid core protein" mean a 99 amino acid protein as is shown in FIG. 2 and fragments thereof such as the 42 amino acid sequence as shown in FIG. 3. Such proteins are also referred to herein as A99 and A42. A 42 amino acid core protein is described by Masters, C. L., et al. *Proc Natl Acad Sci USA* (1985) 82:4245–4249, herein referred to as "Masters, et al."

"A99" is a symbol representing the C-terminal 99 amino acids of the $\beta$-amyloid precursor and is considered a "core protein".

"A42" refers to a core protein of the $\beta$-amyloid precursor. The N-terminus is the N-terminus of the 42 amino acid core and therefore contains the entire core domain. As used throughout this application, the term A42 corresponds to the 42 amino acid core sequence of the $\beta$-amyloid precursor protein.

"$\beta$-amyloid related protein" is defined herein as: (1) a 751 amino acid protein as shown in FIG. 1(A–H); (2) a 695 amino acid protein as shown in FIG. 1(A–H) minus the 57 underlined amino acids; (3) the 57 amino acid sequence underlined in FIG. 1(C–D); and (4) analogs of any of (1)–(3) and fragments thereof including, but not limited to, A99 and A42. As an example, this term is used to refer to the protein described by Kang, J. et al., *Nature* (1987) 325:733–736, herein referred to as "Kang, et al." which contains the $\beta$-amyloid core protein within its structure at amino acid 597 of a 695 amino acid protein.

"$\beta$-amyloid precursor protein" includes a subgroup of the "$\beta$-amyloid related proteins" defined above. Such precursor proteins were first disclosed by "Kang et al." and are produced naturally as larger precursors proteins of the "$\beta$-amyloid core protein"; the 751 amino acid sequence is the most notable example of a precursor protein as used in connection with the invention.

"Immunogenic $\beta$-amyloid core peptide" or "immunogenic $\beta$-amyloid-related peptide" refer to peptides whose amino acid sequences match those of some region of the $\beta$-amyloid core protein or $\beta$-amyloid precursor protein, and which are capable of provoking an antibody response in an immunized animal. Examples of such proteins are described in detail by Kitaguchi et. al., *Biochemical and Biophysical Research Communications,* Vol. 166, No. 3, Feb. 14, 1990.

"Genetic predisposition to Alzheimer's disease" refers to an identifiable genetic mutation or alteration found in the genomes of individual's with Alzheimer's disease, or those individuals destined to develop Alzheimer's disease, but not normal (nondiseased) individuals.

"A4i" as used herein refers to the 57 amino acid sequence underlined in FIG. 1(C–D). The "A4i" may be a polypeptide corresponding to the novel serine protease inhibitor encoded by the polynucleotide derived from the bacteriophage $\lambda$APCP168i4. The A4i polypeptide is not necessarily physically derived from the expression product of this bacteriophage, but may be generated in any manner, including peptide synthesis, recombinant DNA techniques or a combination thereof.

"Corresponding" means homologous to or substantially equivalent to the designated sequence.

"Genetic material" is a material containing any DNA sequence or sequences either purified or in a native state such as a fragment of a chromosome or a whole chromosome, either naturally occurring or synthetically or partially synthetically prepared DNA sequences, DNA sequences which constitute a gene or genes and gene chimeras, e.g., created by ligation of different DNA sequences. Genetic material does not include DNA sequences incorporated in or carried by a plasmid, virus or phage.

"Exogenous genetic material" is a genetic material not obtained from or does not naturally form a part of the specific germ cells or gametes which form the particular zygote which is being genetically transformed.

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Gene" is the smallest, independently functional unit of genetic material which codes for a protein product or controls or affects transcription and comprises at least one DNA sequence.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype.

"Zygote" is a diploid cell having the potential for development into a complete organism. The zygote can result from parthenogenesis, nuclear transplantation, the merger of two gametes by artificial or natural fertilization or any other method which creates a diploid cell having the potential for development into a complete organism. The origin of the zygote can be from either the plant or animal kingdom.

"Parthenogenesis" is any technique that allows for the development of a female or male gamete into a cell and its development into an organism, which technique is different from the natural development of female and male gametes.

5.2. Disclosure Overview and Organization

In order to disclose and describe this invention in an organized fashion, particular aspects of the invention are described in different sections. The definition of terms has been given above in Section 5.1.

The following Section 5.3 describes the various DNA sequences which express different proteins, precursor proteins, and inhibitors, as well as promoter sequences which are fused to these sequences in order to obtain expression of the protein in particular tissues. These DNA sequences are described in part by biological deposits made in connection with this disclosure and by reference to the attached figures.

Section 5.4 of the disclosure describes protocols by which it was possible to confirm that the sequence described in Section 5.3 could be expressed to produce proteins.

Figure 4B:
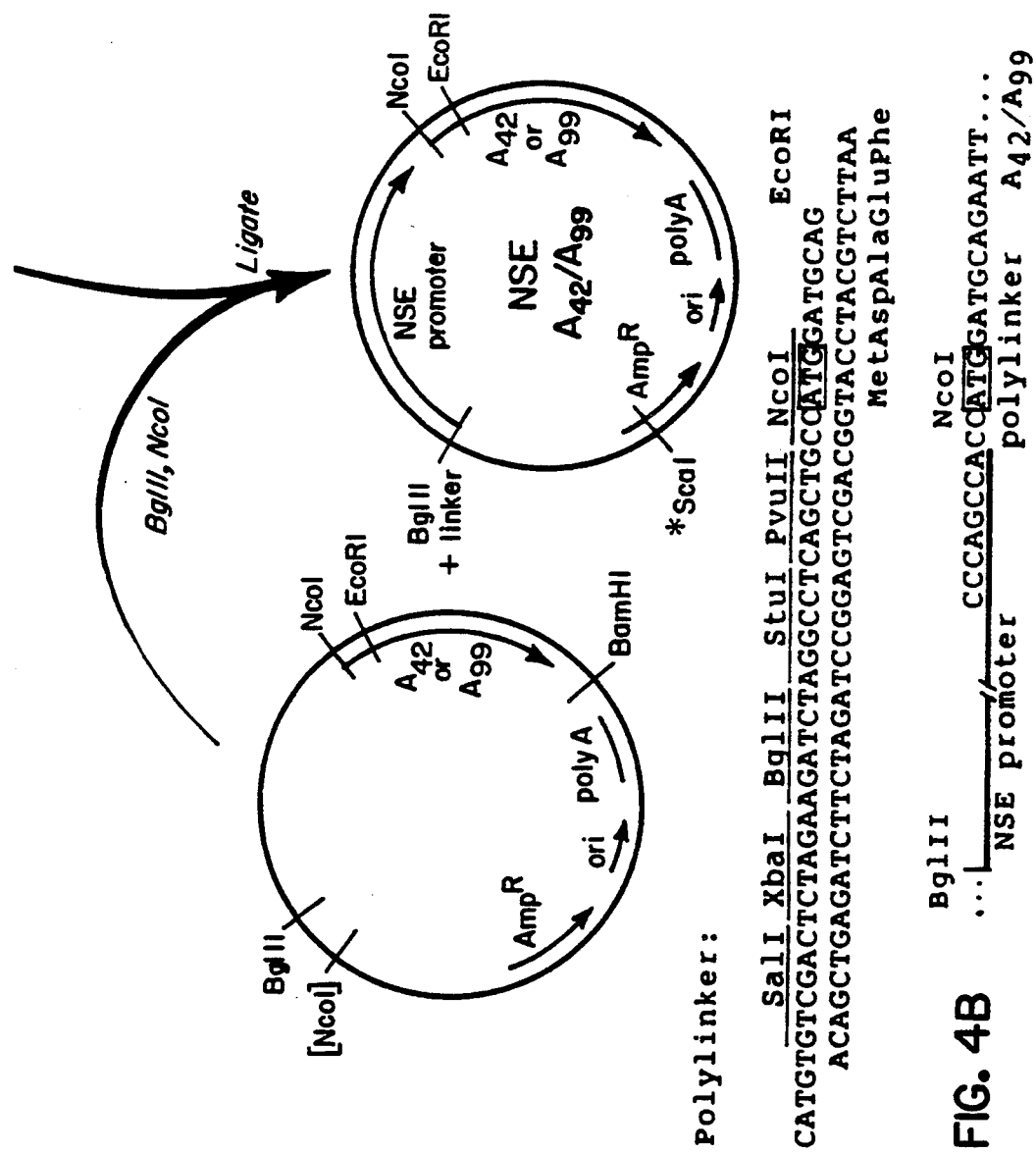
Figure 5A:
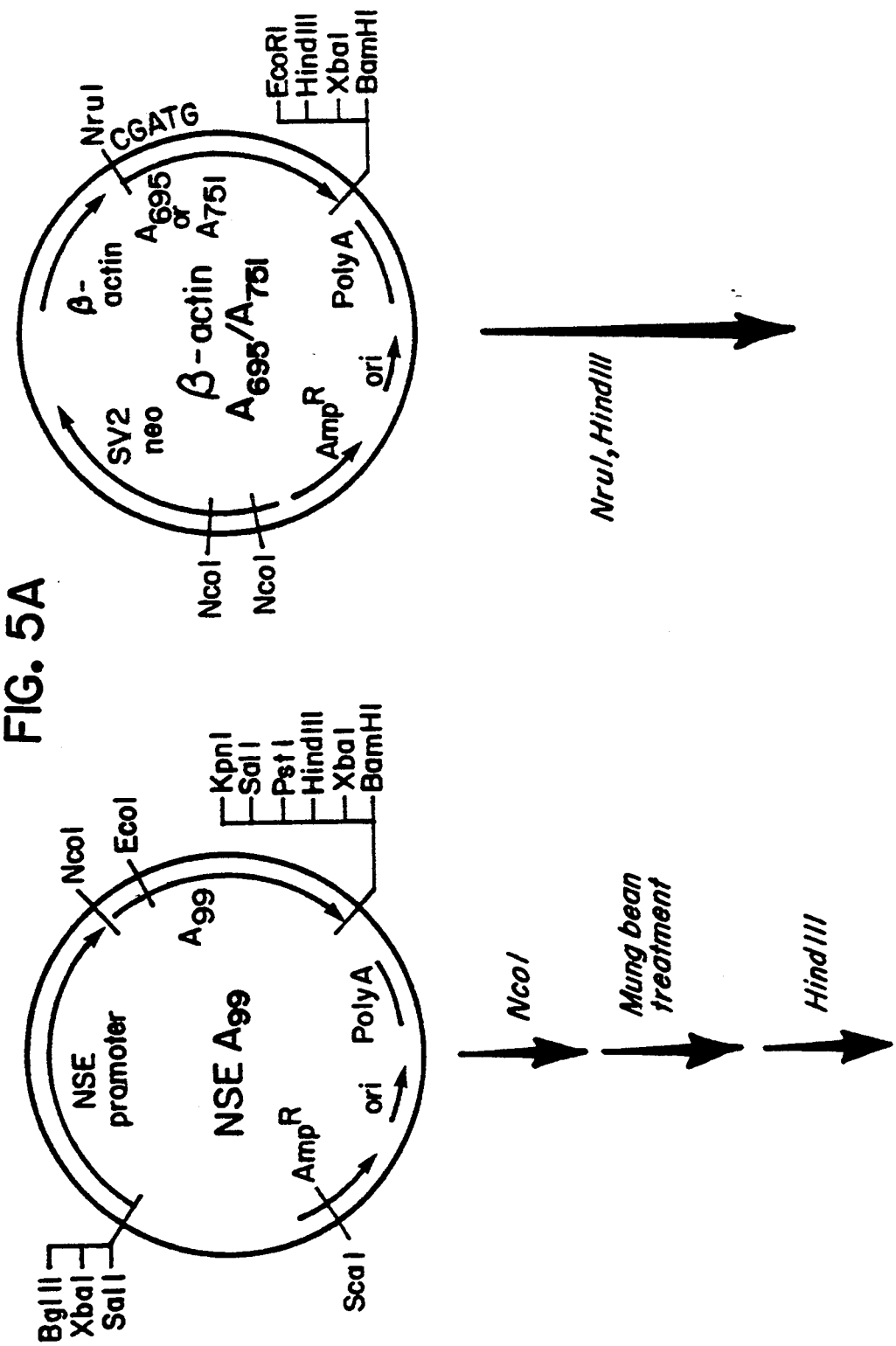
FIG. 5(A–B) shows the construction strategy for the NSE promotor linked to A695 and to A751.
Figure 5B:
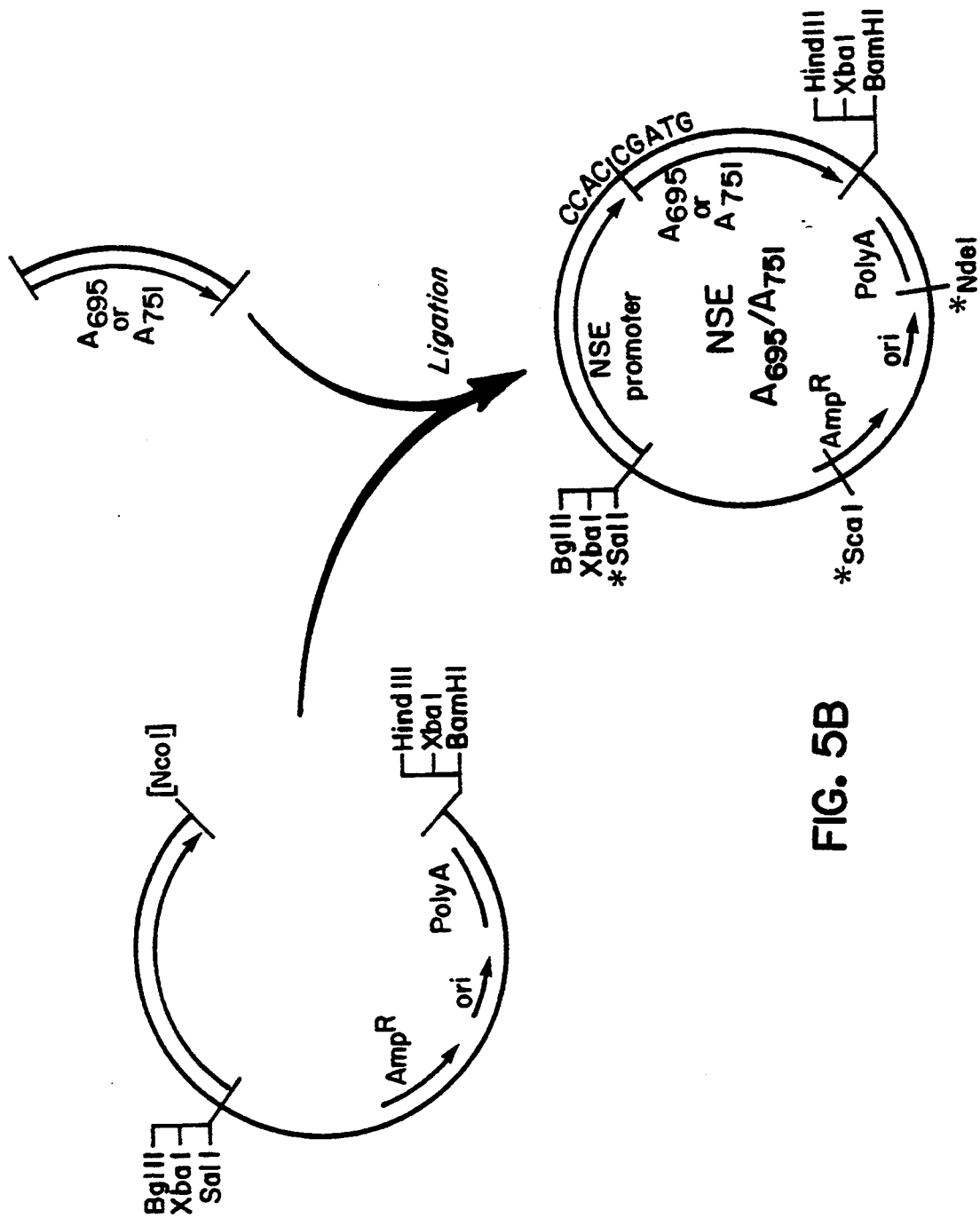
Figure 6A:
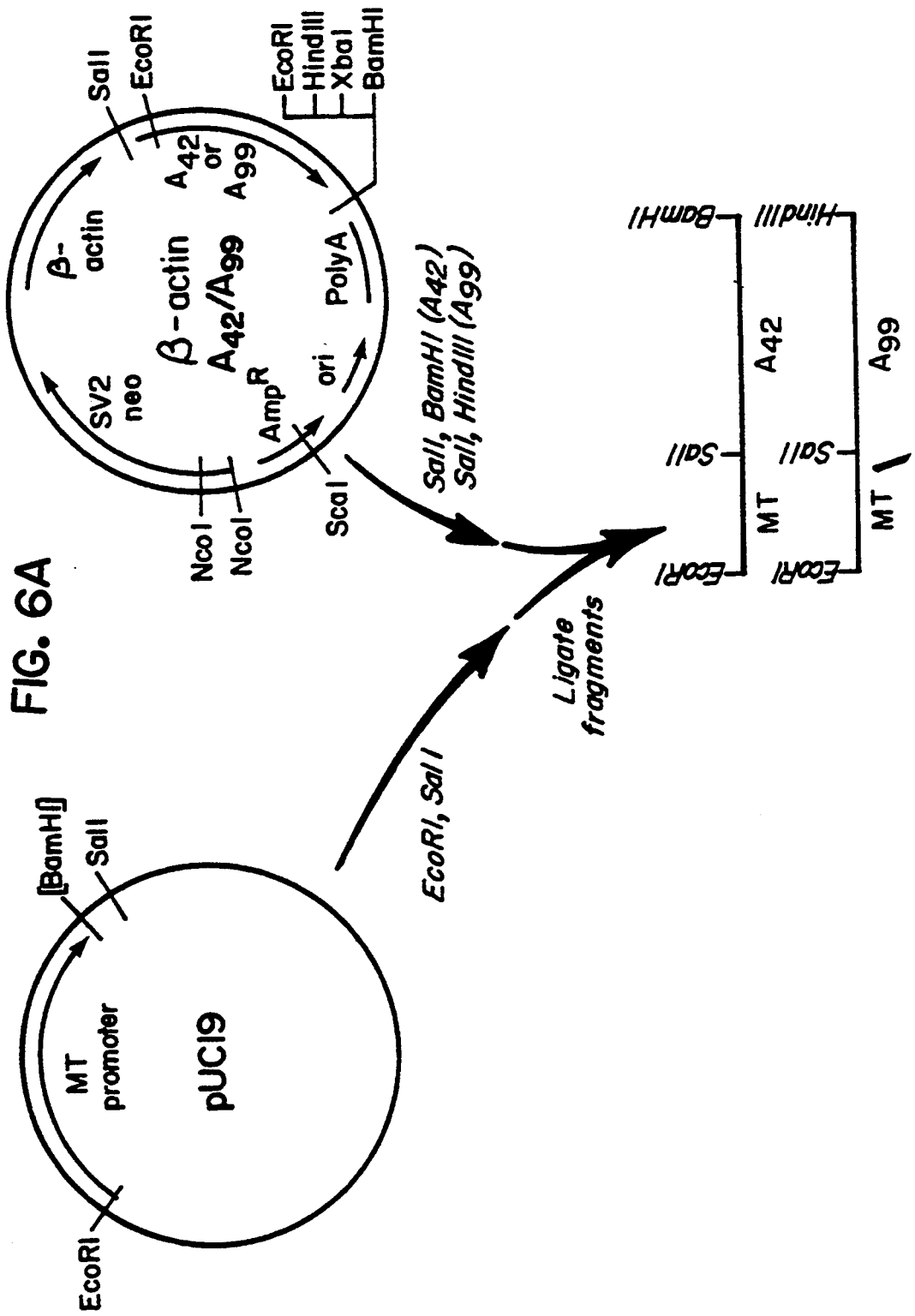
FIG. 6(A–B) shows the construction strategy for MT promotor linked to A42 and to A99.
Figure 6B:
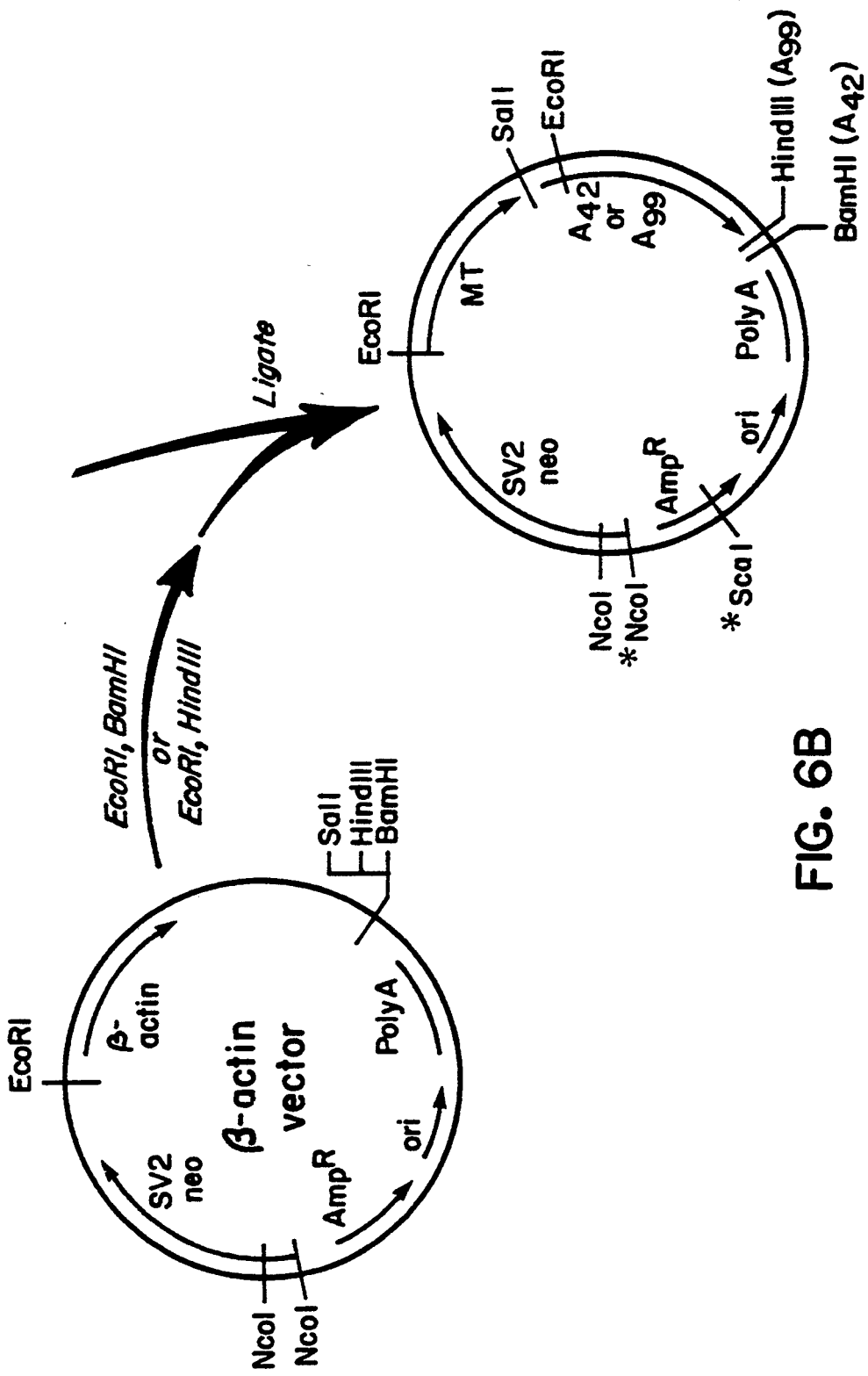
Figure 7A:
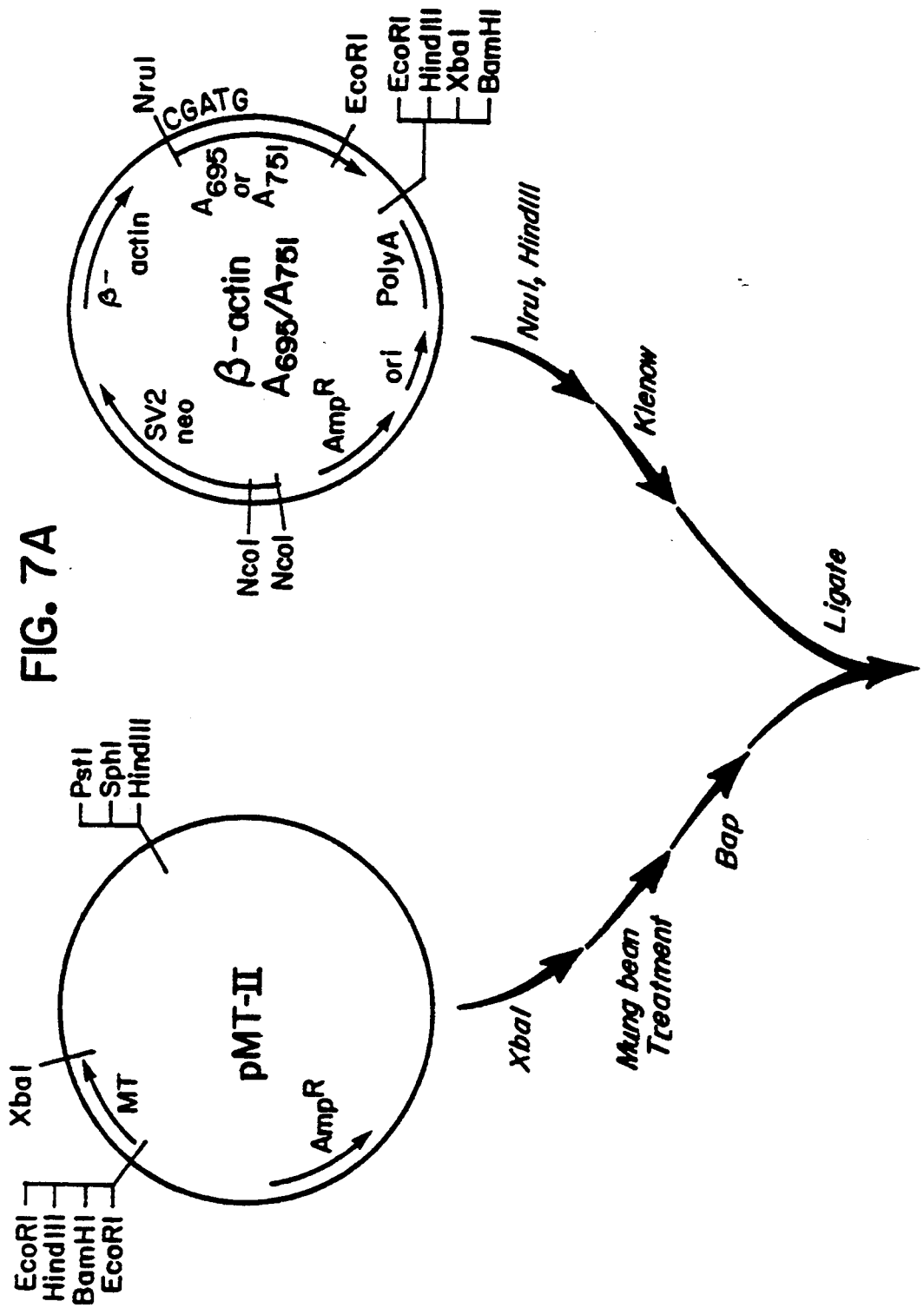
FIG. 7(A–B) shows the construction scheme for a mammalian cell expression vector for the expression of MT-A751 and MT-A695.
Figure 7B:
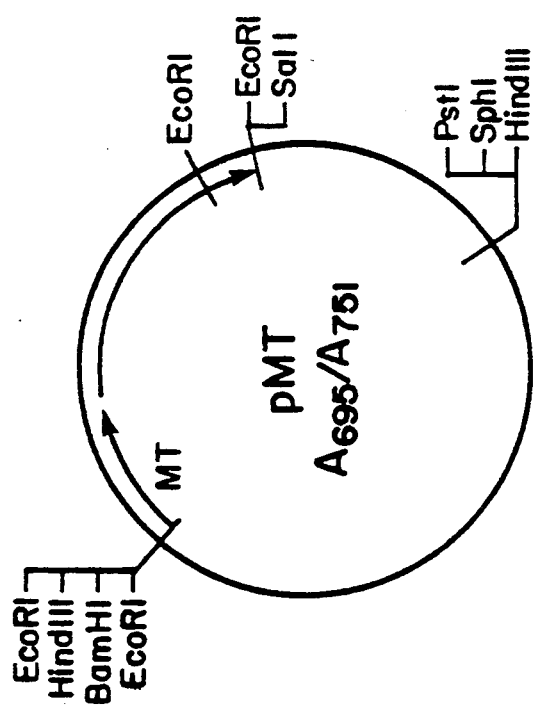

Section 5.5 describes eight different promoter/A4 sequence constructs and, with reference to FIGS. 4(A-B), 5(A-B), 6(A-B) and 7(A-B) describes the synthesis of the constructs.

Section 5.6 describes methods of producing the transgenic mice of the invention utilizing the DNA sequences, constructs and other information described in the above sections.

Various methods and materials used in connection with the different aspects of the invention are described in Section 5.7.

Detailed Examples, the Claims and Abstract follow.

5.3. DNA Sequences

In order to describe the transgenic mice of the present invention, it is necessary to describe certain DNA sequences. For example, it is important to describe the DNA sequence which encodes a β-amyloid precursor protein comprising the nucleotide sequence and corresponding, deduced amino acid sequence set forth in FIG. 1(A-H). This DNA sequence encodes an approximately 82,610 dalton protein containing β-amyloid-related core protein.

As a first step toward producing the transgenic mice of the present invention, the β-amyloid protein cDNA sequence, set forth in FIG. 1(A-H), can be obtained in any manner known to those skilled in the art. One method of obtaining A751 is by isolating it from bacteriophage containing the cDNA clone λAPCP168i4. This human fibroblast cDNA clone known as λAPCP1-68i4 was deposited at ATCC on Jul. 1, 1987 and has accession No. 40347.

The 168 basepair insert (underlined in FIG. 1(C-D) interrupts the codon for $Val_{289}$ of the Kang et al. sequence, resulting in the loss of this amino acid from the λAPCP168i4 protein. The 168 basepair insert, together with the 3 basepairs gained from the interrupted $Val_{289}$ codon, encode 57 new amino acids, which are underlined in FIG. 1(C-D). Downstream of this insertion, at codon 653 of FIG. 1G lies the amino-terminal aspartate of the β-amyloid core protein described by Masters et al.

A unique feature of the transgenic mice of the present invention relates to including cell specific promoters in front of sequences which encode A42, A99, A695, A751 and A4i (note that A4i is the 57 amino acid insert found in λAPCP168i4).

The ability of the transgenic mice to selectively express these particular peptides (in specific types of cells), including any fragments thereof, distinguishes the present transgenic mice from others.

The cloned recombinant and/or synthetic DNA sequences used in connection with the present invention are sequences which are encoded for the production of a biologically active, refolded protein, which protein is preferably selected from the group consisting of:

| A4 Name | Description | Sequence in Fig. |
|---------|-------------|------------------|
| A42 | β-amyloid core domain | 3 |
| A99 | β-amyloid carboxy tail | 2 |
| A695 | β-amyloid precursor protein | 1 (A-H) |
| A751 | precursor plus inhibitor | 1 (A-H) |
| A4i | protease inhibitor | 1 (C-D) |

The A4i is underlined in FIG. 1(C-D) and mice which incorporate a sequence which expresses A4i generally or in specific cells are part of the present invention (i.e., notwithstanding cell specific promoters) as the A4i protein may itself be a valuable compound in preventing or reducing the effects of Alzheimer's disease. Transgenic animals containing sequences expressing A4i are not heretofore known.

5.4. Protein Production

Preferred cDNA clones used in making the transgenic mice include coding sequences which may be expressed to obtain any one of A42, A99, A695, A751 and A4i. These sequences are first inserted in a suitable expression vector for replication and to confirm production of protein.

Briefly, an E. coli expression vector, designated pAPCP118-3, was constructed for the expression of a fusion protein consisting of amino acid residues 655 to 751 set forth in FIG. 1(G-H). The construction of pAPCP118-3 was accomplished by joining the following three fragments: (1) a plasmid backbone (consisting of pBR322 replication functions, an ampicillin resistance gene, the tryptophan promoter and operator, a ribosome binding site, DNA encoding the seven amino terminal codons of the β-galactosidase structural gene followed by six threonine residues, and transcription termination signals); (2) an EcoRI-HaeII fragment encoding amino acid residues 655-728 of the FIG. 1(G-H) sequence; and (3) a synthetic fragment encoding amino acid residues 729-751 of the FIG. 1H sequence, followed by a stop codon.

The resulting vector was used to transform E. coli W3110 and expression of the fusion protein was induced by reducing the tryptophan concentration followed by the addition of 3-β-indoleacrylic acid. The resulting protein can be purified using conventional purification techniques and the resulting purified material is available for use in the production of antibodies for diagnostic assays.

The complete coding sequence of the β-amyloid precursor protein set forth in FIG. 1(A-H) was subcloned in two fragments from the deposited λAPCP1-68i4 clone and prepared for insertion into pSC11 or pUV1 vaccinia virus expression vectors. Briefly, an approximately 1.06 kilobase (kb) EcoRI fragment, spanning amino acid residues 655-751 of the protein illustrated in FIG. 1(G-H), was cloned into EcoRI-digested plasmid pGEM-3 ™ (available from Promega Biotec) to create an intermediate vector designated p4BI. Subsequently p4BI was digested with HindIII to remove much of the 3' noncoding sequence of the β-amyloid-related sequence. The resulting vector p4BWRI was digested with EcoRI and treated with calf intestinal alkaline phosphatase prior to ligation to the 2088 bp EcoRI fragment derived from λAPCP168i4 to form p4T4B. This plasmid was digested with SmaI and XmnI to generate a 2678 bp fragment spanning the complete protein encoding sequence set forth in FIG. 1(A-H).

The gene encoded by this SmaI-XmnI fragment was inserted into one of the two well-known vaccinia viral vectors, pSC11 and pUV1, for subsequent expression of the β-amyloid precursor protein in CV-1 monkey kidney cells using a eucaryotic transient expression system as described by Cochran, M. A., et al., Proc Natl Acad Sci USA (1985) 82/2:19-23. More commonly, these vectors are used for in vivo protein and antibody production in animals after its sequences have been inserted into the vaccinia virus genome.

Figure 10:
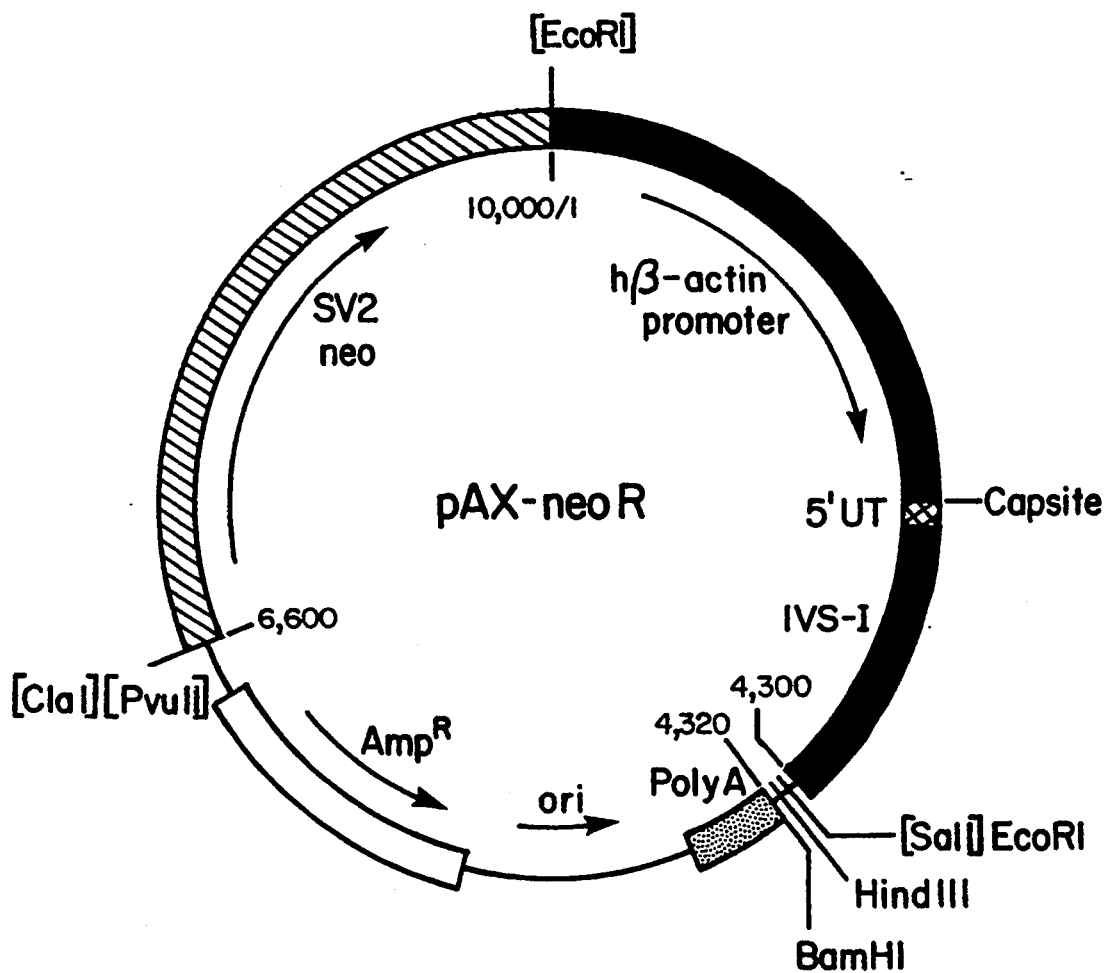
FIG. 10 shows a construction scheme for a mammalian cell expression vector for β-amyloid expression/selection of β-amyloid core constructs.

Similarly, mammalian vectors can be utilized for expression of the β-amyloid core protein or β-amyloid precursor proteins described herein. A useful mammalian vector utilizing human β-actin as a promoter is shown within FIG. 10. The details with respect to a description of the vector shown within FIG. 10 are as follows:

Base pairs 1–4300 are the 4.3 kb EcoRI-AluI fragment from the human β-actin gene isolate p14Tβ-17 (Leavitt et al., Mol. Cell. Biol. (1984) 4:1961–1969)

For sequencing details of the promoter, see Ng et al., Mol. Cell. Biol. (1985) 5:2720–2732. The cap site, 5' untranslated region and IVS 1 positions are indicated. There is no ATG codon present in the 5'UT nor in the poly-linker region from the 3' splice site to the BamHI site.

Base pairs 4300–4320 are in part derived from pSP64 poly-linker (Melton et al., Nucl. Acids Res. (1984) 12:7035–7056).

Base pairs 4320–6600 are derived from pcDV1 (Okayama & Berg, Mol. Cell. Biol. (1983) 3:280–289) and contains the pBR322 Amp$^R$ gene and bacterial origin plus the SV 40 late region polyadenylation signal.

Base pairs 6600–10000 are the PvuII-EcoRI fragment from pSV2-neo (Southern & Berg, J. Mol. App. Genet. (1982) 1:327–341) containing the bacterial neo gene linked to the SV 40 ori plus early promoter. Direction of transcription is as indicated. The vector can be used for efficient protein expression in Chinese hamster Norg (CHO) cells.

An example of another potentially useful vector is plasmid phGH-SV(10) (a plasmid described in EPA 217,822, published Apr. 15, 1987, and incorporated herein by reference) contains a pUC8 plasmid backbone, hMT-IIa gene promoter and regulator elements, SV 40 DNA promoter and enhancer elements, and the coding portions of the hGH gene and 3' regulatory sequences. This plasmid can be digested with BamHI and SmaI and treated with BamHI linkers to delete the human growth hormone protein encoding sequence and leaving the 3'-noncoding sequences and regulatory elements attached to the plasmid backbone. This approximately 5100 base pair DNA piece is gel purified and ligated to BamHI linkers.

Digestion with BamHI, repurification of the DNA fragment and subsequent ligation result in a plasmid designated pMTSV40 polyA Bam which contains the structural and regulatory elements comprising a mammalian cell expression vector. After BamHI digestion of pMTSV40 polyA BamHI and repair in the presence of DNA polymerase I and all four dNTPs, this vector is available for insertion of the ~2678 bp SmaI-XmnI restriction fragment of plasmid p4T4B. The vector can then be used for efficient protein expression in CHO cells.

5.5. Promoter/A4 Sequence Fusion Constructs

Eight different fusion constructs were prepared by fusing one of two different promoters to different DNA sequences which code for β-amyloid precursor proteins. The promoter sequences used were mouse metallothionein-I (MT) and rat neural-specific enolase (NSE). These promoters or other useful promoters known to those skilled in the art can be linked to various A4 sequences of the type described above.

Some useful neural-specific promoters which can be used to create constructs and inserted into transgenic mice in connection with the present invention are as follows:

(1) Neurofilament M or L promoters. These promoters demonstrate a high level of expression and are found in connection with the most abundant neural protein. They are characterized by CNS/PNS neuronal-specific expression and have been used in connection with transgenic expression. The mouse gene for this promoter is a published sequence and the isolation of the promoter region is necessary in order to use the promoter in connection with the present invention.

(2) Glial fibrillary acidic protein (GFAP) promoter sequences. Such promoters are characterized by murine specificity and CNS/PNS glial-specific expression. The promoter has been characterized and is available.

(3) Growth associated protein 43 (GAP 43) is also characterized by CNS/PNS neuronal-specific expression. The promoter is expressed developmentally and upon induced injury. The promoter within a rat has been characterized and is available.

(4) Nerve growth factor (NGF) promoters are characterized by PNS developmental expression and CNS maintained expression in the hippocampus and cortex which are the same areas afflicted by Alzheimer's disease. The mouse gene promoter is published and isolation of this promoter is possible and necessary for use in connection with the present invention.

(5) The JC Virus T antigen can be used. The human papilloma virus has neuronal tropism. The TAg promoter is characterized and is available.

(6) pp60$^{c-src}$ demonstrates 10× higher expression levels in CNS as compared with its expression in non-neuronal cells. The regions of the CNS expression are confined to specific brain regions and the promoter has been characterized.

(7) N-CAM—Neural cell adhesion molecule demonstrates murine neuronal-specific expression.

While not wishing to be bound to any particular theory regarding the pathology of Alzheimer's disease, it is postulated that the ratio of the amount of A751 to the amount of A659 precursors which are unique to the nervous system may be in a state of imbalance, giving rise to Alzheimer's pathology. This imbalance (resulting from over- or under-expression of one precursor) might create a condition for amyloid to form in abundance and create the plaques. Based on this theory, constructs were designed to express either the A751 or A695 β-amyloid protein precursors.

Alternatively, Alzheimer's pathology may result from inadequate or incomplete catabolism of the carboxy tail of the β-amyloid precursor protein (A99 sequences) which is released when A695 and A751 are processed to soluble extracellular proteins (see Weidemann, A., et al., Cell. (1989) 57:115–126). Based on this theory, constructs were designed to express the carboxy tail (A99) or the β-amyloid core protein (A-42). All constructs were designed to permit expression of the construct either specific to neural tissues (NSE) or ubiquitously expressed in all types of tissue (MT promoters).

The following fusion constructs are preferred examples of constructs useful in connection with the present invention:

| Promoter | A4 Sequence | Figure |
| --- | --- | --- |
| NSE | A42 core domain | 4 (A-B) |

| Promoter | A4 Sequence | Figure |
|---|---|---|
| NSE | A99 carboxy tail | 4 (A-B) |
| NSE | A751 | 5 (A-B) |
| NSE | A695 | 5 (A-B) |
| NSE | A4i | |
| MT | A751 | 6 (A-B) |
| MT | A695 | 6 (A-B) |
| MT | A42 core domain | 7 (A-B) |
| MT | A99 carboxy tail | 7 (A-B) |
| MT | A4i | |

As indicated above, FIGS. 4(A-B), 5(A-B), 6(A-B), 7(A-B) and 10 detail the cloning strategies used for producing the different fusion constructs. It should be pointed out that β-actin A42 and β-actin A99 plasmids served as the source for the A42 and A99 sequences, respectively, for the constructions. Complete coding fidelity was maintained in the A42 and A99 constructs; each was simply preceded by a methionine initiator codon.

The β-actin A751 and β-actin A695 vectors were used to prepared the other NSE promoter constructs. All of the plasmid constructions have been confirmed by restriction map analysis. All of the constructs have been definitively confirmed by DNA sequence analysis of the cloning junctions.

The MT-I promoter used for the fusion constructs was derived using synthetic oligonucleotides. The MT-1 promoter is sequenced and described in detail by Swanson, L. W. et al., Novel Developmental Specificity in the Nervous Systems of Transgenic Animals Expressing Growth Hormone Fusion Genes, *Nature* (1985) 317:363-366, incorporated herein by reference to describe the MT-I promoter. The MT-I promoter region encompasses 373 basepairs and can be constructed by synthesis and ligation of DNA oligomers.

Five pairs of oligomers 70-80 nucleotides in length are used. The resultant 373-basepair fragment can be cloned and sequenced. The MT-I promoter can also be isolated by selectively amplifying this region of the mouse genome using the polymerase chain reaction (PCR) method. The amplified fragment can be cloned and characterized by DNA sequence analysis.

Two different approaches can also be used to isolate the rat neuronal-specific enolase promoter (NSE). The nucleotide sequence of the promoter region has been published. Accordingly, it is possible to design synthetic oligonucleotides for use in PCR and for screening genomic libraries. Oligonucleotide primers were used to selectively amplify the region of interest using PCR and rat genomic DNA. A 1.15 kilobasepair fragment was isolated and cloned. The same oligonucleotide has been employed as a probe to screen rat genomic libraries.

The MT-I promoter was proven functional by assessing the transient expression of a construct bearing the CAT reporter gene (that is, the reporter gene chloramphenicol acetyltransferase), after transfection of the DNA into CHO cells.

The NSE promoter can also be isolated from a genomic clone purified from a buffalo rat DNA library using oligonucleotide probes designed from the published sequence of the promoter (Sakimura et al., *Gene* (1987) 60:103-113) which is incorporated herein by reference to disclose such a promoter.

Figure 9C:
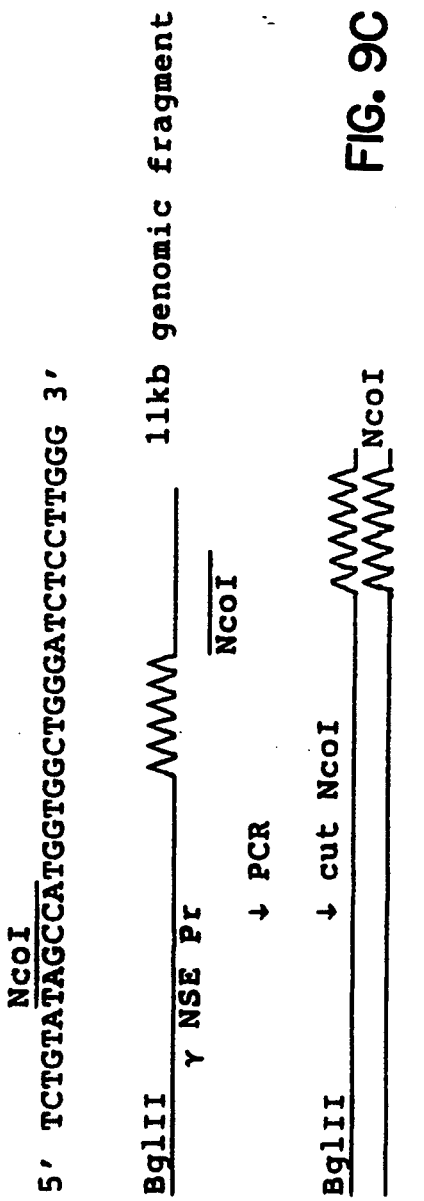
FIG. 9(A–C) shows the NSE promoter sequence and a PCR Amplification Scheme for NSE.

A promoter region fragment of 2.3 kilobases including a 1.2 kilobase intron in the 5'-untranslated region was prepared from an 11 kb clone using polymerase gene reaction amplification. The PCR strategy and oligonucleotide primers used are described in FIG. 9(A-C). The 3'-terminal primer for the NSE promoter fragment plus intron-harbored 2 nucleotide substitutions to create a NcoI site for cloning purposes, as well as to introduce the initiator methionine codon for the A4 sequences. It is pointed out that polymerase chain reaction amplification is reported to have a low error rate.

5.6. Transgenic Organisms

The transgenic organisms of the invention all include within a plurality of their cells a cloned recombinant or synthetic DNA sequence which is believed to relate to the pathogenesis of Alzheimer's Disease. More specifically, the transgenic organisms contain specific sequences of exogenous genetic material, such as the sequences described above in detail which are comprised of a tissue specific promoter sequence and a sequence which encodes for production of a β-amyloid precursor protein. Since it is possible to produce transgenic organisms of the invention utilizing one or more of the above-described sequences, a general description will be given of the production of transgenic organisms by referring generally to exogenous genetic material. This general description can be adapted by those skilled in the art in order to incorporate the above-described specific DNA sequences into organisms and obtain expression of those sequences utilizing the methods and materials described below. For more details regarding the production of transgenic organisms, and specifically transgenic mice, refer to U.S. Pat. No. 4,873,191, issued Oct. 10, 1989 (incorporated herein by reference to disclose methods producing transgenic mice), and to the numerous scientific publications referred to and cited therein.

The exogenous genetic material may be placed in either the male or female pronucleus of the zygote. More preferably, it is placed in the male pronucleus as soon as possible after the sperm enters the egg. In other words, right after the formation of the male pronuclei when the pronuclei are clearly defined and are well separated, each being located near the zygote membrane. The male pronucleus of a fertilized mouse egg is the preferred site for addition of the exogenous genetic material of the present invention.

It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material could then be added to the ovum or the decondensed sperm could be added to the ovum with the exogenous genetic material being added as soon as possible thereafter.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the DNA sequences which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of a gene, in order to insure that one copy is functional. As regards the present invention, there is generally an advantage to having more than one functioning copy of each of the inserted exogenous DNA sequences to enhance the phenotypic expression of the exogenous DNA sequences (i.e., to obtain ubiquitous expression of the $\beta$-amyloid related precursor proteins and protease inhibitor proteins).

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

The transgenic mammals produced in accordance with the present invention will include exogenous genetic material. The exogenous genetic material will be a DNA sequence which results in the production of a $\beta$-amyloid related protein. Further, the sequence will be attached to a promoter which promoter preferably allows the expression of the $\beta$-amyloid related protein in a specific type of cell such as a nerve cell and may include a promoter which allows expression within a particular type of nerve cell.

In some preferred embodiments of the invention the transgenic animal includes a cell specific promoter in connection with a DNA sequence which results in the production of a $\beta$-amyloid precursor protein. A number of examples of such precursor proteins are disclosed and described. As a particularly preferred example of a transgenic mammal of the invention there is provided transgenic mammals which include DNA sequences capable of producing all or any of the proteins as described above in Section 5.5. The sequences are preferably included in connection with a promoter as also shown within Section 5.5. However, other promoters which allow for cell-specific expression and particularly nerve cell-specific and still more particularly certain types of nerve cell-specific expression are preferred embodiments of the invention. In yet another preferred embodiment of the invention the transgenic mammal includes a sequence which is capable of producing the A4i protein. This unique sequence may be produced in connection with all types of promoters. Transgenic mammals containing sequences capable of expressing A4i proteins were not known prior to the present invention. Particularly preferred embodiments of the invention include sequences capable of producing such A4i proteins which sequences are connected to cell-type specific promoters such as nerve cell-specific promoters and still more particularly in connection with particular types of nerve cell-specific promoters.

5.7. Methods and Materials

Most of the techniques which are used to transform cells, construct vectors, extract messenger RNA, prepare cDNA, and the like are widely practiced in the art, and most practitioners are familiar with the standard resource materials as well as specific conditions and procedures. However, for convenience, the following paragraphs may serve as a guideline.

5.7.a. Hosts and Control Sequences

Both procaryotic and eucaryotic systems may be used to express the $\beta$-amyloid core and $\beta$-amyloid-related sequences; procaryotic hosts are, of course, the most convenient for cloning procedures. Procaryotes most frequently are represented by various strains of $E.$ $coli;$ however, other microbial strains may also be used. $E.$ $coli$ strains may secrete the $\beta$-amyloid core and $\beta$-amyloid precursor proteins to the periplasm when the genes encoding these proteins are fused to appropriate signal peptides, and certain $E.$ $coli$ strains, for example, a lipoprotein mutant strain such as JE5505 (Kanamari, T. Gene (1988) 66:295–300), will excrete the chimeric proteins directly to the culture medium.

Plasmid vectors which contain replication sites, selectable markers and control sequences derived from a species compatible with the host are used; for example, $E.$ $coli$ is typically transformed using derivatives of pBR322, a plasmid derived from an $E.$ $coli$ species by Bolivar, et al., Gene (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the $\beta$-lactamase (penicillinase) and lactose (lac) promoter systems (Chang, et al., Nature (1977) 198:1056) and the tryptophan (trp) promoter system (Goeddel, et al. Nucleic Acids Res (1980) 8:4057) and the lambda derived $P_L$ promoter and N- gene ribosome binding site (Shimatake, et al., *Nature* (1981) 292:128).

Other procaryotic control sequences include signal sequences which direct secretion of a protein to the periplasm. Commonly used bacterial signal peptides include the ompA (Kikuchi, et al., *Nucleic Acids Res* (1981) 9:5671-5678) and phoA (Beck and Bremer, *Nucleic Acids Res* (1980) 8:3011-3024) signal peptides which can be fused to the protease inhibitor sequence of the invention.

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2 m origin of replication of Broach, J. R., *Meth Enz* (1983) 101:307, or other yeast compatible origins of replication (see, for example, Stinchcomb, et al., *Nature* (1979) 282:39, Tschumper, G., et al., *Gene* (1980) 10:157 and Clarke, L., et al., *Meth Enz* (1983) 101:300) may be used. Control sequences for yeast vectors include promoters for the synthesis of glycolytic enzymes (Hess, et al., *J Adv Enzyme Reg* (1968) 7:149; Holland, et al., *Biochemistry* (1978) 17:4900). Additional promoters known in the art include the promoter for 3-phosphoglycerate kinase (Hitzeman, et al., *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al., U.S. Pat. No. 4,399,216. These systems have the additional advantage of the ability to splice out introns and thus can be used directly to express genomic fragments. Useful host cell lines include VERO and HeLa cells, and CHO cells. Expression vectors for such cells ordinarily include promoters and control sequences compatible with mammalian cells such as, for example, the commonly used early and late promoters from SV 40 (Fiers, et al., *Nature* (1978) 273:113), or other viral promoters such as those derived from polyoma, adenovirus 2, bovine papilloma virus, or avian sarcoma viruses. The controllable promoter, hMTII (Karin, M., et al., *Nature* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA regions. Origins of replication may be obtained, if needed, from viral sources. However, integration into the chromosome is a common mechanism for DNA replication in eucaryotes.

5.7.b. Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the $RbCl_2$ method described in Maniatis, et al., *Molecular Cloning: A Laboratory Manual* (1982) Cold Spring Harbor Press, p. 254 and Hanahan, D., *J Mol Biol* (1983) 166:557-580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al., *Cell* (1979) 16:777-785 may be used.

Transformations into yeast may be carried out according to the method of Beggs, J. D., *Nature* (1978) 275:104-109 or of Hinnen, A., et al., *Proc Natl Acad Sci (USA)* (1978) 75:1929.

5.7.c. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Synthetic oligonucleotides are prepared by either the phosphotriester method as described by Edge, et al., *Nature* (supra) and Duckworth, et al., *Nucleic Acids Res* (1981) 9:1691 or the phosphoramidite method as described by Beaucage, S. L., and Caruthers, M. H., *Tet Lett* (1981) 22:1859; and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM$MgCl_2$, 5 mM dithiothreitol, 1-2 mMATP, 1.7 pmoles $\gamma$32P-ATP (2.9 mCi/mmole), 0.1 mM spermidine, 0.1 mM EDTA.

Once the components of the desired vectors are thus available, they can be excised and ligated using standard restriction and ligation procedures.

Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mMNaCl, 6 mM MgCl$_2$, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 ml volumes under the following standard conditions and temperatures: for example, 20 mM Tris-HCl pH 7.5, 10 mMMgCl$_2$, 10 mM DTT, 33 µg/ml BSA, 10 mM-50 mMNaCl, and either 40 µM ATP, 0.01–0.02 (Weiss) units T4 DNA ligase at 0° C. (for "sticky end" ligation) or 1 mMATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations are performed at 1 mM total ends concentration.

In vector construction employing "vector fragments", the vector fragment is commonly treated with bacterial alkaline phosphatase (BAP) or calf intestinal alkaline phosphatase (CIAP) in order to remove the 5' phosphate and prevent self-ligation of the vector. Digestions are conducted at pH 8 in approximately 10 mM Tris-HCl, 1 mM EDTA using about 1 unit of BAP or CIAP per mg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al., *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

5.7.d. Verification of Construction

In the constructions set forth below, correct ligations for plasmid construction are confirmed by first transforming *E. coli* strain MC1061 obtained from Dr. M. Casadaban (Casadaban, M., et al., *J Mol Biol* (1980) 138:179–207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al., *Anal Biochem* (1981) 114:193–197 and Birnboim, H. C., et al., *Nucleic Acids Res* (1979) 7:1513–1523. The isolated DNA is analyzed by restriction and/or sequenced by the dideoxy nucleotide method of Sanger, F., et al., *Proc Natl Acad Sci (USA)* (1977) 74:5463 as further described by Messing, et al., *Nucleic Acids Res* (1981) 9:309, or by the method of Maxam, et al., *Methods in Enzymology* (1980) 65:499.

6.0 EXAMPLES

The following examples are put forth so as to provide those of ordinary skill in the art with a complete disclosure and description of how to make the DNA sequences, fusion constructs, proteins and transgenic mammals of the invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

6.1 EXAMPLE 1

Expression of β-Amyloid-Related Protein (1–751) in Cultured Mammalian Cells

To facilitate the expression of β-amyloid precursor protein in mammalian cells, a plasmid is constructed such that the coding segment for the protein is fused to a powerful regulated promoter derived from the human metallothionine II (hMTII) gene. This procedure is performed in two steps. First an expression vector pMTSV40 polyA Bam was derived from phGH-SV(10) vector by digestion of phGH-SV(10) with BamHI and SmaI restriction enzymes, followed by incubation with DNA polymerase I (Klenow fragment) in order to create blunt-ended molecules. The blunt ends are subsequently ligated to BamHI linkers, cut with BamHI, and religated to allow for recircularization. This step removes all of the human growth hormone genomic sequence from phGH-SV(10) except for most of the 3' untranslated region of the mRNA and genomic sequences encoding putative 3' transcriptional stop and processing signals. For the mammalian cell expression construct, pMTSV40 polyA Bam is BamHI-digested, then incubated with all four nucleotide triphosphates and with DNA polymerase I to create blunt ends. This fragment is subsequently ligated with the purified 2678 bp SmaI-XmnI fragment derived from p4T4B. The recombinant molecules are introduced into MC1061 by transformation.

CHO-K1 cells are grown in a medium composed of a 1:1 mixture of F12 medium and DME medium with 10% fetal calf serum. The competent cells are co-transformed with the recombinant expression vector and PS V2:NEO (Southern, P., et al., (1982). pSV2:NEO contains a functional gene conferring resistance to the neomycin analog G418. In the transformation, 500 ng of pSV2:NEO and 5 µg of the recombinant vector are applied to a 60 mm dish of CHO cells as a calcium phosphate-DNA co-precipitate as described by Graham, F. L. and Van der Eb, A. J. *Virology* (1973) 52:456–467. Growth of the cells in the antibiotic G418 as described by Southern et al. will yield a pool of stably transfected CHO cells containing expression vector DNA with the capacity to express β-amyloid-related mRNA and protein.

6.2 EXAMPLE 2

Expression of β-Amyloid Precursor in Mammalian Cells

Outlined in Example 1 is the construction of an expression system for the β-amyloid precursor protein (1–751) driven by the human promoter. A nearly identical construct was prepared using the purified 2548 bp SmaIXmnI fragment derived from p4T4B from which 116 bp from the 5' untranslated region have been deleted. This fragment was inserted into the SalI site behind the human promoter on a plasmid harboring the neomycin selectable marker for mammalian cell expression and the ampicillin resistance gene for selection of bacterial transformants. This vector, pHbAPr-1-neo, has been described by Gunning, et al., (*Proc Natl Acad Sci USA* (1987) 84:4831–4835) and has been modified to remove the EcoRI site from the body of the original vector and to substitute the original polylinker region with a new polylinker containing an EcoRI site in addition to the SalI, HindIII, and BamHI cloning sites originally present. The modified vector is referred to as pAXneoR. The pAXneoR vector was linearized with SalI, the termini filled in using Klenow fragment of DNA polymerase to create blunt-ended molecules. The 2548 bp SmaI-XmnI β-amyloid fragment was blunt-ligated into the vector using T4 ligase. The recombinant molecules were introduced into *E. coli* MC1061 by transformation and a clone displaying the proper orientation was amplified. A similar construction was made using the 695 β-amyloid sequences described by Kang et al. (supra) which places the 695 amyloid protein under control of the human promoter.

600 µg total DNA of pAXneo/751 β-amyloid or pAXneo/695 β-amyloid or an equal mass mixture of both plasmid constructs were introduced into $10^7$ CHO cells by electroporation (Neumann, *J Membrane Biol* (1972) 10:279–290; Zimmerman, *Biophys J* (1973) 13:1005–1013) using a BTX Transfector 100, Bio-Rad sterile, disposal cuvettes and a custom built cuvette holder. G418-resistant cells receiving the exogenous DNA were selected by standard protocols (Southern, 1982, supra) using 500 82 g/ml G418 from Gibco.

The pool of positively transfected cells resistant to G418 from each of the three transfections was characterized with respect to β-amyloid precursor protein expression. Approximately $2 \times 10^6$ cells from each pool containing 5 ml of serum-free medium were incubated at 37° C. for 48 hr. The conditioned media was removed and the protein precipitated by addition of trichloroacetic acid to a final concentration of 10%. Cells were harvested by scraping, washed in saline buffered with phosphate and resuspended in 50 µl of buffer for a 30-fold concentration. 25 µl of each sample was loaded onto a 12.5% polyacrylamide gel (Laemmli, *Nature* (1970) 277:680–685). The β-amyloid precursor was detected by Western blot analysis (Towbin, *Proc Natl Acad Sci USA* (1979) 76:4350–4354) using β-amyloid-specific polyclonal antibodies generated by recombinant vaccinia virus harboring the β-amyloid 751 cDNA by using standard procedures. Typically, the majority of the approximately 110,000 dalton β-amyloid precursor is found to be released into the culture media and very small amounts of the protein are cell-associated. This result is in keeping with the hypothesis of Allsop, et al., (*Proc Natl Acad Sci USA* (1988) 85:2790–2794) proposing that the β-amyloid protein is a secreted prohormone. The apparent molecular weight of 110,000 daltons of the recombinantly expressed β-amyloid protein is similar to that observed by others (Dyrks, T., et al., *EMBO J* (1988) 7(4):949–957) using in vitro transcription/translation systems and using cells in culture (Weidemann, A., et al., *Cell* 57, 115–126 (1989).

6.3 EXAMPLE 3

Assay to Distinguish Genetic Variants of β-Amyloid-Related Protein mRNA Species

The ability to distinguish between genetic variants of β-amyloid precursor protein mRNA species using oligonucleotide probes is demonstrated herein. This diagnostic assay can distinguish between two closely related genetic variants of β-amyloid precursor proteins or their mRNAs, and quantitate the relative levels of expression of these proteins or mRNAs.

Total cellular RNA or cytoplasmic RNA was prepared from human cells in culture or human brain tissue (Alzheimer's brain or normal brain) with or without removal of nuclei (cytoplasmic or total, respectively) by the guanidine thiocyanate/CsCl method as described by Maniatis et al. RNA was fractionated by oligo-dT cellulose chromatography, electrophoresed on a formaldehyde agarose gel, and blot-transferred to nitrocellulose (all as described in Maniatis et al.) Filters were baked, prehybridized and hybridized to the indicated probes according to standard protocols.

Oligonucleotide probes were end-labeled with [$^{32}$P]-dCTP by incubation with terminal transferase according to manufacturer's suggestions and as described by Ponte et al. *Nature* 331:525–527 (Feb. 11, 1988) which is incorporated herein by reference to disclose such end-labeling. Actin insert was radiolabeled with [$^{32}$P]-CTP by nick-translation. After hybridization, the filters hybridized to oligonucleotides were washed at $1 \times$ SSC, 55° C. The filter hybridized to actin was washed at 0.1 $\times$ SSC at 55° C. Filters were then exposed to X-ray film to produce the autoradiogram shown. The insert probe detects the β-amyloid precursor protein mRNA described in FIG. 1(A–H) in all samples examined. The junction probe detects the β-amyloid-related mRNA described by Kang et al. in all cells except HeLa and MRC5. The actin probe is a control which is expected to hybridize to an abundant RNA in all cells.

6.4 EXAMPLE 4

Construction of the NSE-A42 and A99 Transgenic Expression Plasmids

A42 and A99 sequences were derived from the β-actin A42 and A99 expression plasmids described in U.S. patent application Ser. No. 07/408,767. Specifically, the β-actin A42 and the beta-actin A99 plasmids were digested with NcoI and EcoRI releasing the β-actin promoter region as well as the SV2 neo promoter region. In addition, by digesting with EcoRI, five amino acids of A42 or A99 were removed which can be replaced using a synthetic polylinker. The A42 or A99 plasmid deleted for the β-actin and SV2 neo promoters was purified by agarose gel electrophoresis. A synthetic oligonucleotide polylinker which generates multiple cloning sites as well as the five amino acids for A42 and A99 was synthesized and ligated to the A42 or A99 plasmid fragment generated earlier by NcoI and EcoRI digestion. Addition of the polylinker deletes the NcoI site in the original plasmid and moves this site to within the polylinker, and replaces the EcoRI site within the A42 or A99 sequences. After ligation of the polylinker to the A42 or A99 plasmid fragment, plasmid DNA was prepared. The new plasmid was next cleaved with BglII and NcoI. Both of these sites were synthesized into the newly added polylinker region. It is in the site generated by BglII-NcoI digestion that the NSE promoter will be added.

The NSE promoter was isolated from a rat genomic library. An 11 kb genomic EcoRI fragment was selected using hybridization with oligonucleotides designed from the known NSE promoter region sequence. The 11 kb genomic EcoRI NSE promoter fragment was cloned into a pUC plasmid and it was from this genomic fragment that the desired promoter region was isolated using PCR amplification as outlined in FIG. 9(A-C). A large portion of the promoter region containing an intron in the 5' untranslated region of the NSE gene was produced by PCR amplification using oligonucleotide primers with BglII and NcoI restriction sites at the 5'- and 3'-termini, respectively. The NSE promoter fragment was purified by gel electrophoresis and then cloned into the BglII-NcoI polylinker region of the A42 or A99 plasmid generated earlier. Standard molecular recombinant techniques were used to digest, ligate and isolate the fragments. DNA sequencing documented the fidelity of the NSE-A42 and NSE-A99 expression plasmids.

6.5 EXAMPLE 5

Construction of the NSE-A695 and the NSE-A751 Transgenic Expression Plasmids

The NSE-A99 plasmid made in Example 4 was used to prepare NSE-A695 and NSE-A751 expression plasmids by removing the A99 sequences and replacing them with either A695 or A751 sequences. To remove the A99 sequences from the NSE-A99 plasmid, the plasmid was digested with NcoI followed by mung bean nuclease digestion. The mung bean nuclease treatment generates a blunt end at the NcoI site for further cloning purposes. The plasmid was next digested with HindIII. This site is within the polylinker region 3' to the A99 sequences causing the release of the A99 coding fragment. The remaining plasmid containing the NSE promoter, the plasmid sequences, the poly A addition site, and part of the polylinker region was purified by gel electrophoresis. Next, the A695 and the A751 fragments were prepared for cloning into the A99-deleted NSE plasmid. The A695 and the A751 sequences were derived from β-actin A695 and β-actin A751 expression plasmids. To remove the 695 and 751 sequences, the plasmids were digested with NruI and HindIII. The NruI site is immediately 5' to the initiating methionine codon of 695 and 751. The HindIII site is located in the polylinker region 3' to the termination codon of 695 and 751. The NruI-HindIII fragment containing A695 or A751 sequences was cloned into the blunted NcoI-HindIII treated A99-deleted NSE plasmid. The final plasmids, NSE-A695 and NSE-A751, were documented as correct by DNA sequencing of the cloning junctions. These plasmids were proven to express 695 and 751 protein after transfection into mammalian cells.

6.6 EXAMPLE 6

Preparation of the Metallothionein A42 and Metallothionein A99 Transgenic Expression Plasmids A synthetic metallothionein I mouse promoter designed from the published sequence was prepared using oligonucleotide synthesis and ligation. The synthetic metallothionein or MT promoter was cloned into pUC19. To prepare the MT-A99 and the MT-A42 transgenic expression plasmids, the A42 and the A99 sequences were isolated from the β-actin A42 and A99 expression plasmids, respectively. The A42 and A99 sequences were excised from the β-actin expression plasmid using digestion with SalI and BamHI for A42 and SalI and HindIII for A99. The SalI site common to A42 and A99 is 5' to the initiating methionine of A42 and A99. The BamHI site and the HindIII sites are both contained in the polylinker region 3' to the A42 and A99 coding sequences. The SalI-BamHI fragment for A42 and the SalI-HindIII fragment for A99 were purified by gel electrophoresis. The synthetic MT promoter fragment was isolated by digestion of the pUC plasmid with EcoRI and SalI. The EcoRI-SalI MT promoter fragment was ligated with the SalI-BamHI A42 fragment. Similarly, the EcoRI-SalI MT promoter fragment was ligated to the SalI-HindIII fragment of A99. The MT promoter-A42 and the MT promoter-A99 fragments were then cloned into a plasmid backbone for a complete expression plasmid. The plasmid backbone used is the parent β-actin vector from which the modified pAXneoR plasmid was derived. The plasmid vector was prepared for cloning by digestion with EcoRI and BamHI for insertion of the RI-BamHI-MT-A42 fragment or the plasmid backbone was digested with EcoRI and HindIII for insertion of the EcoRI-HindIII-MT-A99 fragment. Standard methodologies for recombinant DNA manipulation were used to create the plasmids. The MT-A42 and MT-A99 transgenic expression plasmids were verified as correct in sequence by DNA sequence analysis.

6.7 EXAMPLE 7

Construction of MT-A751 and MT-A695 Transgenic Expression Plasmids

A promoter plasmid was constructed using the synthetic MT-1 fragment earlier described. This plasmid also contains SV 40 termination region possessing an intron. Between the promoter and the SV 40 termination sequences, there exists an XbaI site. The plasmid was cut at this XbaI site then treated with mung bean nuclease to create a blunt end. It is in the blunted XbaI site of the MT plasmid that the 751 and 695 sequences will be inserted. 695 and 751 complete coding sequences were derived from the β-actin 695 and the β-actin 751 expression plasmids. To obtain this fragment the β-actin expression plasmids were digested with NruI and HindIII. The NruI site is immediately 5' to the initiator methionine of A695 and A751. The HindIII site is located 3' prime to the termination codon of A695 and A751 within the polylinker region of the plasmid. Digestion with NruI creates a blunt terminus. Digestion with HindIII creates a sticky end which was filled in with Klenow to make a blunt ended fragment at both the 3' and 5' termini of 695 and 751. The 695 and the 751 blunt end fragment was cloned into the blunted XbaI metallothionein SV 40 plasmid. The resulting MT-A695 and MT-A751 plasmids were documented as correct in sequence at the cloning junctions by DNA sequence analysis.

Figure 11A:
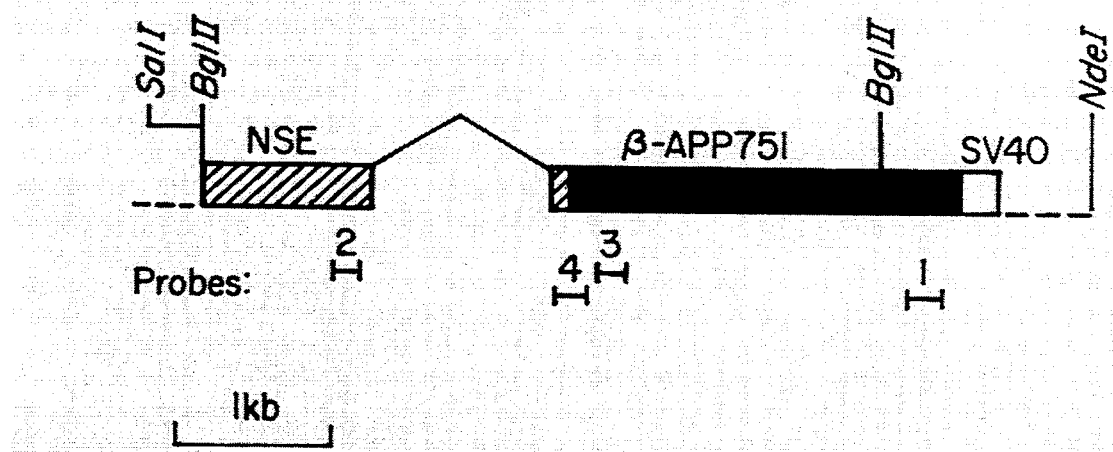
FIG. 11A shows a schematic diagram of the transgene NSE-A751.

FIG. 11A shows a schematic diagram of NSE-A751 transgene. The 2.3 kb NSE promoter and associated 5'-untranslated region is indicated by the cross-hatched box. The intron within the NSE DNA is indicated by lines. A751 sequences are represented by the solid box. The SV40 late region 3'-untranslated region containing polyadenylation signals is indicated by the open box. Dashed lines define plasmid sequences. Restriction endonuclease sites, as well as probes (1–4) used for Southern blot and reverse transcriptase PCR analyses are indicated.

6.8 EXAMPLE 8

Collecting and Injecting the Eggs 6.8.a. Procedure

Fertilized ova were collected from the oviducts of JU female mice previously mated with males. The ova were collected at an early pronuclear stage wherein the male and female pronuclei are separated and distinguishable within the cytoplasm. The collected ova were separated from any surrounding cells and materials, properly washed and stored in accordance with procedures known to those skilled in the art. The zygotes were preferably stored in a depression slide containing culture medium overlayered with paraffin oil in an atmosphere of 5% carbon dioxide, 5% oxygen, and 90% nitrogen (percentages are based on volume) at 37° C.

A fusion construct of NSE with 5' intron connected to A751 was obtained in accordance with the procedure described above and shown within FIG. 9(A–C). Any of the above-mentioned fusion constructs can be cloned and included within a fertilized ovum in a manner as described herein. Accordingly, the following is a specific description with respect to A751 but is a generalized procedure applicable with any of the abovedescribed fusion constructs.

First, the fusion constructs were cloned as schematically shown within FIG. 10. After cloning, the fusion constructs were extracted from the host, purified and then digested with the appropriate nuclease in order to remove as much of the undesired bacterial sequences as possible. The extracted plasmids are purified by cesium chloride ethidium bromide density gradient centrifugation followed by extraction of the ethidium bromide and dialysis of the plasmid DNA. After carrying out such extraction and purification processes on any of the cloned sequences, it is possible to obtain relatively purified plasmids containing the desired fusion constructs.

The purified plasmids were then treated with the appropriate endonuclease (SalI and NdeI were used to obtain linear fragments of NSE-A751 or NSE-A695). By utilizing gel electrophoresis the desired fragments were isolated by the use of Gene Clean glass beads (sold by Bio 101, San Diego, Calif.) followed by filtration through a 0.22μ membrane.

Purified DNAs obtained were microinjected utilizing injection pipettes with an external diameter of about 1 μl. Such pipettes can be prepared from Pyrex tubing as described in Proc. Natl. Sci. U.S.A., 74:5657–5661 (1971). Approximately ten picoliters of the solution containing the fusion constructs (which is approximately 20,000 DNA sequences) was drawn into an injection pipette. The zygote was positioned on a holding pipette which has an external diameter of about 60 to 70 microliters, which pipette can also be prepared in accordance with the procedure of the above-cited publication. The zygote was positioned on the holding pipette so that the male pronucleus was injected with the fusion constructs present in the injection pipette.

All of the zygotes were microinjected, then placed in culture tubes where they were allowed to develop for five days. Suitable conditions for preimplantation development are described within Biol. Reprod. 8:420–426 (1973). Ova which developed to morulae or blastocytes were transplanted into the uteri of $F_1$ hybrid JU, foster mouse mothers who were at day 3 of pseudopregnancy. These foster mothers carried the implanted embryos to term.

Injection techniques of the type described above and of the type known to those skilled in the art were utilized in order to inject embryos with different conjugates of the invention as shown below within Table 1, wherein experiments 1–5 were carried out using the different conjugates on different numbers of mouse embryos. The expected and actual results of these experiments are tabulated within Table 1 which shows the number of mouse eggs injected, the number of live pups which resulted from the implantation of those eggs and the number of pups which actually turned out to be transgenic, that is, which actually turned out to incorporate the foreign DNA which were injected into the embryos.

TABLE 1

|  |  | EXPERIMENTS | | | | |
|---|---|---|---|---|---|---|
|  | EXPECTED | #1 NSE/695 | #2 NSE/695 | #3 NSE/751 | #4 NSE/99 | #5 MT/99 |
| EMBRYOS INJECTED | 200 | 289 | 148 | 233 | 236 | 288 |
| LIVE PUPS | 20–40 (10–20%)! | 7(2.4%) | 7(4.7%) | 44(19%) | 28(12%) | 25(8.7%) |
| TRANSGENIC ANIMALS | 2–8 (10–20%)* | 3(43%) [1%] | 1(14%) [0.6%] | 9(20%) [3.8%] | 3(11%) [1.3%] | 3(12%) [1.0%] |

TABLE 1-continued

| | EXPERIMENTS | | | | |
|---|---|---|---|---|---|
| EXPECTED | #1 NSE/695 | #2 NSE/695 | #3 NSE/751 | #4 NSE/99 | #5 MT/99 |
| [1–4%]** | | | | | |

! % of embryos resulting in live pups.
* % of live pups who are transgenic.
** % of embryos injected resulting in live transgenic animals.

The transgenic mice obtained by experiments 1–5 as shown in Table 1 above are useful in determining the effectiveness of a drug in decreasing the amount of plaques formed as a result of Alzheimer's disease. Transgenic mice from any one of the experiments can be used in comparison with control mice which are nontransgenic or various combinations of the transgenic mice can be compared with each other and/or with the controls with the object being determining the effectiveness of one or more drugs in decreasing the amount of plaques formed and thus relating the decrease in the plaques with the effectiveness of the drug in treating Alzheimer's disease.

EXAMPLE 9

Determination of Transgene Copy Numbers

For the following examples, results are described for embryos and mice injected with NSE-A751 DNA.

Figure 11B:
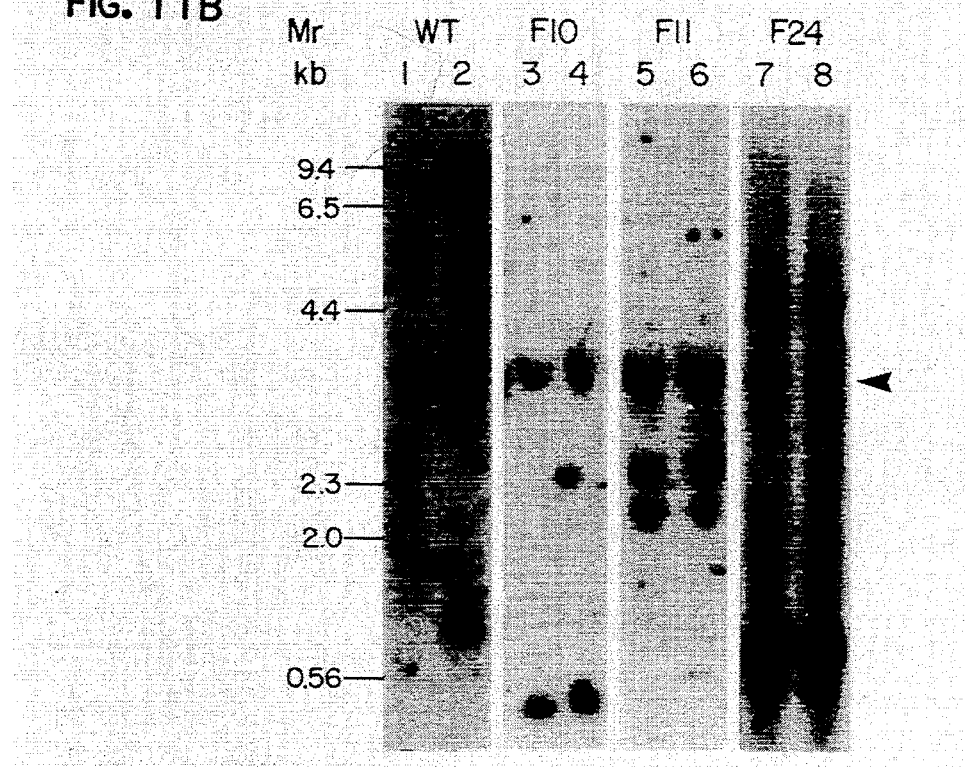
FIG. 11B is a black and white photograph of Southern blots of DNA taken from wild-type and transgenic mice.

As indicated in Table 1, 9 of 44 mice that developed from embryos injected with NSE-A751 DNA carried the transgene. Breeding of these mice resulted in the establishment of 8 lines; the transgene of one founder was not inherited by progeny. Three pedigrees were selected for further characterization, including founder 10 (F10), founder 11 (F11) and founder 24 (F24). (Table 2). Transgene copy numbers were estimated by comparison to the endogenous single copy b-APP mouse gene using Southern blot hybridization with an oligonucleotide probe common to both mouse b-APP and human b-A751 (FIG. 11B). Forty mg of tail DNA was digested with BglII and electrophoresed on an 0.8% agarose gel. Southern blots were prepared and hybridized with an oligonucleotide probe (FIG. 11A, probe #1; 5'-GGATGTGTACTGTTTCTTCTTCA-3') radiolabeled with 32P by T4 kinase.

Blots were hybridized at 60° C. in 6 × SET (1×SET=0.15M NaCl, 30 mM Tris-HCl pH.0, 2 mM EDTA) with 5 ×Denhardt's solution and washed at 60° C. for 40 minutes in 6 × SSC (1× SSC=0.15M NaCl, 0.15M Na citrate). F10, F11, and F24 lines had approximately, 1, 4, and 8 copies of NSE:b-A751 per haploid genome, respectively.

6.8.b. Analysis

Two different approaches to identify transgenic NSE-A751 and NSE-A695 progeny were used. These methods are polymerase chain reaction (PCR) and Southern blot analysis. High molecular weight DNA was prepared from a section of mouse tail (0.5–1.3 cm). For PCR, two synthetic oligonucleotides were prepared; one, a 21mer (5'TCAGTGGGTAC-CAGCGCC3'), is located within the intron of the NSE promoter, the other, a 21mer (5'CACTGGCCT-CAGGCTCCACCC3'), is located within the coding region of A751/695. When both oligos are used to amplify transgenic DNA carrying either NSE-751 or NSE-695, a 148 basepair DNA should result. No such DNA is predicted to be amplified from DNA lacking the exogeneous DNAs.

The fidelity and sensitivity of these oligos were tested by performing PCR on mouse tail DNA which had been spiked with 1, 10, 100 picograms of NSE-751 DNA. As predicted, a 148 basepair DNA sequence was obtained with all spiked DNA samples but was absent in the untreated control DNA. The 148 basepair DNA was further characterized using restriction endonuclease digestion with StyI and BglII, sites known to exist in this 148 basepair region of each construct. Cleavage of the amplified 148 basepair DNA with these enzymes produced fragments of the expected molecular weights. It is possible to readily detect 1 picogram of foreign DNA with PCR. Since approximately 8 picograms of NSE-A751/695 DNA in 5 μg mouse genomic DNA is equivalent to 1 gene copy it is feasible to detect a single transgenic. The PCR amplification method has proven to be highly reliable in identifying transgenic progeny.

For the second approach, a 30 base oligonucleotide was synthesized which bridges the junction of the NSE promoter and the precursor sequences (5'AGATC-CCAGCCACCGATGCTGCCCGGTTTG3'). No such sequence should naturally exist in the mouse genome except those harboring exogeneously added NSE-751/695. Using this oligo as a probe, Southern blots of mouse tail DNA (spiked with NSE-A751 DNA and untreated) can also be used to identify transgenic animals. This method has been proven to work to identify transgenic animals and is additionally useful to determine the approximate copy number of the exogeneously added gene in each transgenic animal.

EXAMPLE 10

RNA Expression of Inherited Transgenes

RNA expression of inherited transgenes was studied in three pedigrees. Two mg of total brain RNA was isolated from positive and wild-type control animals, reverse transcribed with oligo dT12-18, and a specific DNA subfragment amplified by polymerase chain reaction (PCR). The reaction was divided into 2 aliquots.

Oligonucleotide primers for the PCR were designed such that only transcripts derived from the transgene would be amplified, i.e., one primer hybridized to the NSE 5'-untranslated region (5'-CACCG-CCACCGGCTGAGTCTGCAGTCCTCG-3') and the other the 5'-coding domain of the b-APP (5'-TCTTGCACTGCTTGCGGCCCCGCTTGCACC-3'). To account for contaminating genomic DNA or unprocessed transcripts, the NSE PCR primer corresponded to a site located upstream from the intron. A predicted 373 basepair fragment was amplified from reverse transcribed DNA prepared from each transgenic animal, but was not amplified from reverse transcribed RNA isolated from wild-type mice. As a control, the second aliquot of the reversed transcribed RNA was amplified with a primer for native b-APP secretory signal (5'-TTGGCACTGCTCCTGCTGGCCGCCTGGACG-3') sequence and the 5'-coding domain b-APP primer described above. In these reactions, both wild-type and transgenic reverse transcribed samples produced the 307 basepair DNA fragment representing amplification from endogenous b-APP RNA.

DNA was electrophoresed on 2% agarose gels, visualized by staining with ethidium bromide, and then Southern blotted and hybridized with a 32P-labeled oligonucleotide probe to the NSE-A751 fusion sequence (5'-AGATCCCAGCCACC-GATGCTGCCCGGTTTG-3').

Blots were hybridized at 65° C. in 6 × SET and washed at 65° C. for 40 minutes in 4 × SSC. When the PCR reaction products were hybridized with the oligonucleotide probe bridging the junction between NSE and b-A751 sequences, only the products derived from the transgenic brains hybridized with the probe, demonstrating the authenticity of the 373 bp PCR product.

EXAMPLE 11

Western Blot Analysis

Changes in protein expression in brains of NSE:b-A751 transgenic animals were determined by Western blot analysis. Protein homogenates were made from total brain according to the methods of Shivers, B. D., et al., *EMBO J* (1988) 7:1365–1370. Fifty mg of each sample was electrophoresed on a 7.5% SDS polyaCrylamide gel and transferred to membranes. Western blots were developed using a 1/500 dilution of polyclonal antiserum raised against full length human A695 expressed by recombinant vaccinia virus and $^{125}$I-protein A. Several bands of about 120 kD corresponding to the reported average size of mammalian brain b-APP isoforms were observed in controls and in each transgenic protein homogenate. Slightly increased levels of b-APP were seen in the NSE-A751 samples relative to wild-type samples suggesting elevated levels of A751 expression in transgenie brains. An accurate assessment of neuronal levels of exogenous A751 expression was difficult to determine, however, due to combined neural and glial expression of endogenous b-APP. Therefore, neuronal levels of exogenous A751 expression were examined by immunocytochemistry of NSE-A751 expression.

EXAMPLE 12

Histological Analysis of Transgenic Mouse Brains with Monoclonal Antibody 4.1

Figure 12A:
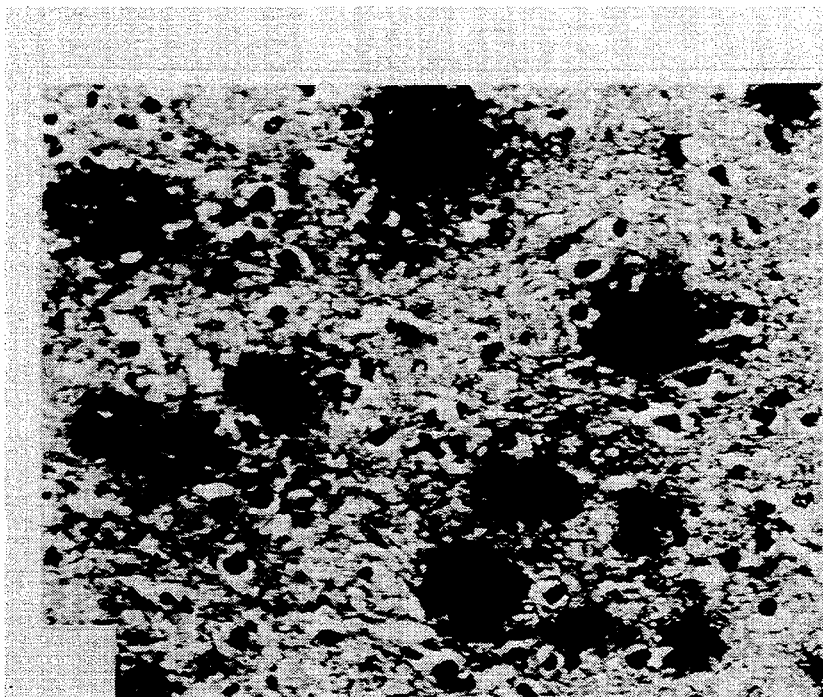
FIG. 12(A–D) show black and white photographs of immunoperoxidase staining of human and mouse brain.
Figure 12B:
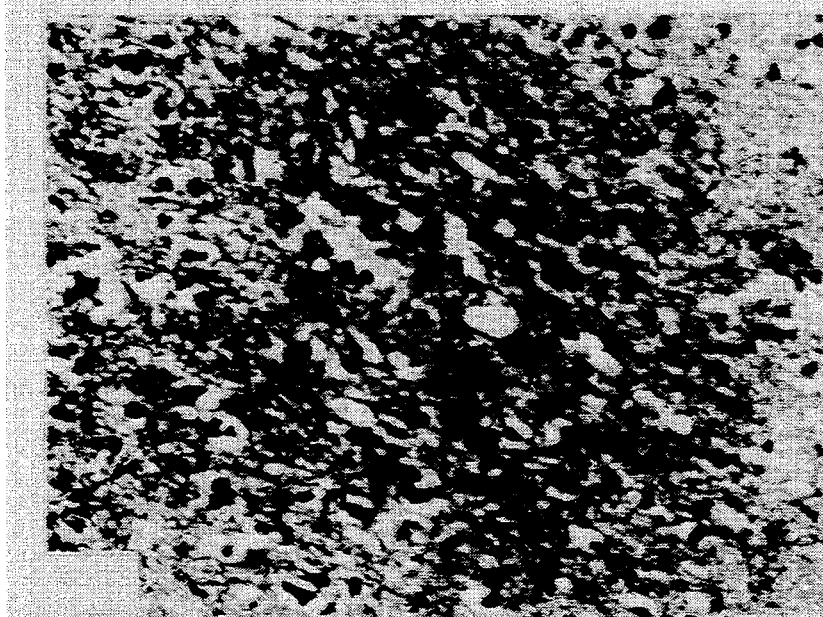

Monoclonal antibody 4.1 was used for histological analysis of transgenic mouse brains. This antibody recognizes an epitope which has been mapped to the N-terminal 10 residues of the β-amyloid protein and has high affinity and specificity for neuritic plaques. Any immunoreactivity was eliminated by preincubating the monoclonal antibody with the synthetic peptide immunogen prior to staining. Briefly, a synthetic peptide corresponding to residues 1–28 of the β-amyloid protein was prepared and self-aggregated by freezing and thawing. The peptide aggregate was mixed with methylated bovine serum albumin and adjuvant for immunizing and boosting mice. Hybridomas from sensitized spleen cells were generated. Clones secreting anti-peptide antibodies were expanded and subcloned by limiting dilution. Brains of NSE-A751 transgenic mice, wild-type mice, and homozygotic and hemizygotic animals from three transgenic lines were analyzed (Table 2). Brains were removed and mixed with 4% paraformaldehyde, embedded in paraffin and 6 mm coronal midbrain sections were made. Sections were deparaffinized, rehydrated, treated for 30 minutes with 0.3% $H_2O_2$, then with 80% formic acid for about 2 minutes. Sections were then incubated at 37° C. for 30 minutes with 1/20 dilution of conditioned medium from the hybridoma secreting 4.1 antibody. An anti-mouse avidinbiotinylated horseradish peroxidase (ABC) kit was used according to the manufacturer's suggestion (Vector, Burlingame, Calif.), and the horseradish peroxidase visualized with 3,3'-diaminobenzidine. Sections were counterstained with hematoxylin and eosin. For staining of full-length b-APP, a 1/400 dilution of antiserum raised against full-length human b-APP695 expressed by recombinant vaccina and an anti-rabbit ABC kit was used. Sections were counterstained with hematoxylin and eosin. Human brain sections were obtained from individuals clinically diagnosed with Alzheimer's disease. Human sections were prepared and stained identically as mouse tissue sections except they were treated with 98% formic acid for 10 minutes. For competition experiments, the antibody diluent was preincubated at 4° C. for 12 hours at 37° C. for 30 minutes with 250 mg/ml 1–28 β-amyloid synthetic peptide prior to application. As shown in FIG. 12A and 12B, the antibody selectively stains neuritic plaques in human tissue section and immuoreactivity is eliminated by preincubating the monoclonal antibody with the synthetic peptide immunogen prior to staining.

Transgenic and wild-type brain sections were stained in parallel with the 4.1 antibody. Greater amounts of immunoperoxidase reactivity were observed in neurons and throughout the neuropil of transgenic brains compared with brains from wild-type mice.

Figure 12C:
Figure 12D:
Figure 13A:
FIG. 13 (A–E) show black and white photographs of photomicrographs of immunoreactive deposits in NSE-A751 brains.
Figure 13B:
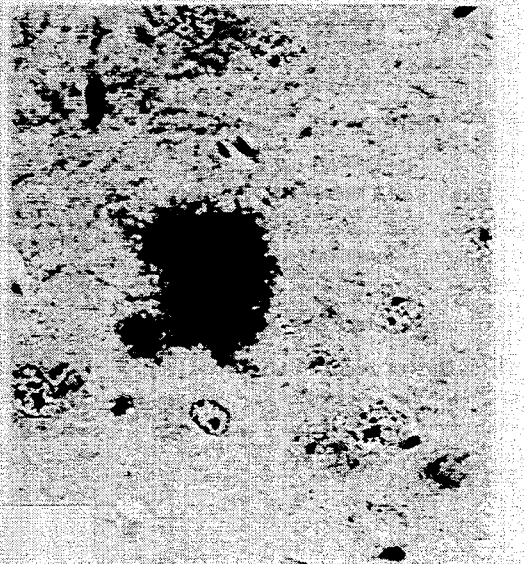
Figure 13C:
Figure 13D:
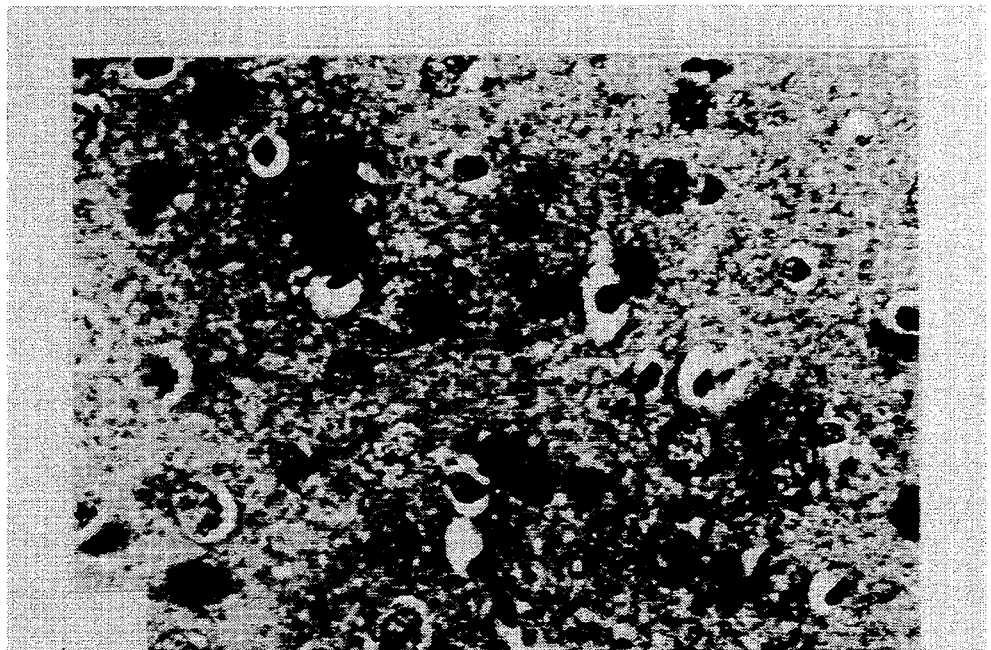
Figure 13E:

FIG. 12C shows an example of increased neuronal staining in the hippocampal pyramidal cell layer from an animal of NSE-A751 founder 10 pedigree (FIG. 12C). Significant staining of neuritic processes was also observed. Enhancement of arborizing neuronal process was most evident in stratum flanking the pyramidal cell layer of the CA-1 and CA-3 regions of transgenic hippocampi. Enhanced staining of neuritic processes in the deeper cortical layers of transgenic brains was also seen. Neuronal and process staining was fully competed by prior incubation of the antibody with the 28 residue synthetic β-amyloid peptide and was decreased by formic acid treatment.

Extracellular immunoreactive deposits were also seen in brain sections from the three transgenic lines stained with the 4.1 monoclonal antibody (FIG. 13(A–D). These deposits are not seen in wild-type animals studied. The deposits vary in size, shape, and frequency. Compact deposits of 10–30 mm in diameter are shown in FIG. 13(A–E). Deposits were observed most frequently in the cortex and hippocampus although they occasionally were seen in the thalamus and striatum. The deposits tend to occur in clusters. On the average 5 deposits were seen in a single whole brain section from NSE-b-A751 founder 10 or 11, however, fifteen 10–50 mm sized deposits have been observed in a single section. Amorphous or granular immunoreactive extracellular deposits were also seen in transgenic brains section stained with the 4.1 monoclonal antibody and not in control brain sections. FIG. 13G shows an example of diffuse β-amyloid immunoreactivity in the hippocampus of an animal from NSE-b-A751 founder 11 line. Detection of extracellular deposits in tissue section from transgenic animals required treatment with formic acid. Staining of the structures was competed by the β- amyloid peptide as seen in FIG. 13E. Deposits stained variable with antibodies raised to full length b-APP. Brains from NSE-A751 founders 10 and 11 displayed a greater number of compact deposits than NSE-b-A751 founder 24 (Table 2) even though founder 24 has more copies of the NSE-bA751 transgene.

TABLE 2

Summary of Mice Employed for Immunohistology

| Line | Animal | Sex | Age[1] | Genotype | Copy #[2] | Deposits[3] |
|---|---|---|---|---|---|---|
| NSE-751 | | | | | | |
| 10 | 0 | F | 12 | Aa | 1 | +++ |
|  | 31* | F | 7 | Aa |  | ++ |
|  | 168 | F | 5 | Aa |  | +++ |
|  | 334 | M | 2 | AA |  | + |
| 11 | 0 | M | 15 | Aa | 4 | +++ |
|  | 51 | M | 12 | Aa |  | + |
|  | 236 | M | 4 | AA |  | +++ |
|  | 287 | F | 3 | AA |  | + |
| 24 | 77 | M | 8 | Aa | 8 | + |
|  | 201 | F | 5 | AA |  | + |
| Wild-type | | | | | | |
|  | 1 | F | 4 | n.a. | n.a | − |
|  | 2 | F | 4 |  |  | − |
|  | 3 | M | 5 |  |  | − |
|  | 4 | M | 3 |  |  | − |
|  | 5 | M | 9 |  |  | − |
|  | 6 | F | 12 |  |  | − |
|  | 7 | M | 14 |  |  | − |

[1]month; [2]haploid; [3]>5 mm in size, (−) (+/++/+++) relative abundance of deposits, i.e., +, <5; ++, 5-10; +++, >10 deposits per section as an average of multiple sections stained. M and F indicate male and female mice, respectively; AA and Aa represent homozygotic and hemizygotic animals, respectively; n.a., indicate not applicable.; *NSE-A751 F10 #31 died spontaneously of unknown cause.

Those mice harboring exogenous genes can be bred to 1) document that the NSE-751 or NSE-695 DNA is stably incorporated into the genome, 2) create a pure line, 3) characterize mRNA and protein expression, 4) ultimately investigate possible pathological consequences of expression of the foreign DNA, and 5) test potential therapeutic compounds.

A variety of analytical procedures can be utilized to identify and characterize transgenic animals produced in accordance with the above-described protocols. It is, of course, necessary to identify which of the transgenic animals include the inserted sequences such as the NSE-A-99, NSE-A-42, MT-A-99 and MT-A-42. These inserts, as well as A4i inserts, can be detected utilizing identical rationale and specific PCR and Southern blotting oligonucleotide reagents and antibodies for Western blotting. A variety of different techniques and combinations of techniques will become apparent to those skilled in the art upon reading this disclosure.

Western blotting methods to identify A751 or A695 precursor in rodent brain have been developed. As an example, a Western blot using antiserum to A695 (raised using the recombinant vaccinia virus system) reacted with total brain homogenate was carried out. A single protein was recognized of 120 kd which is the predicted molecular weight of the precursor. The membrane to which the protein is transferred for the blot greatly influences protein transfer. For proteins of greater than 30 kd, polyvinylenedifluoride (PVDF) is optimal, whereas, below 30 kd, nitrocellulose is more efficient. Other available antisera developed to regions of the amyloid precursor, in particular, sera to the Kunitz inhibitor domain and to the core domain may be used in Western blot analysis of total brain protein. Additionally, by using procedures known in the art, it is possible to isolate monoclonal antibodies to the precursor. Mice have been immunized with a recombinant vaccinia virus which expresses A751 and were shown to raise antibodies to this protein.

FIG. 11B shows a black and white photograph of a Southern blot of DNA from wild-type and transgenic mice. Lanes 1 and 2 , wild-type (WT); lanes 3 and 4, NSE-A751 founder 10 (F10); lanes 5 and 6, NSE-A751 founder 11 (F11); lanes 7 and 8, NSE-A751 founder 24 (F24). The arrow indicates endogenous mouse b-APP gene. Lanes 3-8 of FIG. 11B show additional bonds not present in lanes 1 and 2 which addition bonds indicate exogenous b-APP DNA present in the transgenic mice.

FIG. 12(A–D) shows black and white photographs of immunoperoxidase staining of human and mouse brain. FIGS. 12A and 12B show human Alzheimer's disease tissue section from caudal hippocampus stained with 4.1 antibody without preincubation (12A) and with preincubation (12B) with the β-amyloid synthetic peptide immunogen. FIG. 12C shows pyramidal cell layer of hippocampal CA-1 region of NSE-A751 F10 (#334) stained with 4.1 antibody. FIG. 12D shows the same region from wild-type mouse (#3) stained with 4.1 antibody. Magnification is 500×.

FIG. 13(A–E) shows black and white photographs of photomicrographs of immunoreactive deposits in NSE-A751 brains. FIG. 13A is a compact deposit in frontal parietal cortex of F11 (#0); FIG. 13B is compact deposit in thalamus of F11 (#236); FIG. 13C shows compact deposit in hippocampal CA-2 field of F11 (#0); FIG. 13D shows cluster of deposits in frontal parietal cortex of F10 (#168); FIG. 13E shows amorphous deposits in the hippocampal stratum moleculare of F11 (#236).

7. Uses of the Invention

The transgenic mammals of the present invention are useful in determining the effectiveness of pharmaceutical drugs with respect to their ability to decrease the amount of plaques which form within the brain of the animal. More specifically, the mammals are useful in testing the efficacy of such drugs in preventing the formation or reducing the amount of β-amyloid plaques formed as well as eliminating or reducing plaques already formed.

Methods of producing the transgenic animals of the invention have been described above. Once produced, a drug to be tested is administered to a control animal or group of animals which are not the transgenic animals of the invention and simultaneously to transgenic animals of the invention. The drug is preferably continuously administered over a period of time which is normally sufficient to effect the deposition of amyloid protein deposits in the brain of the animal. After administering the drug for a sufficient period of time the control animal(s) along with the transgenic animal(s) are sacrificed. Examination of the brain of the animals is made. By comparing the amount of deposits within the control animal(s) to the amount of deposits within the transgenic mammal(s) of the invention a determination can be made with respect to the effectiveness of the drug in controlling the relative amount of amyloid deposits.

In that the transgenic animals of the invention can be used to test the efficacy of drugs with respect to preventing amyloid deposits the animals are valuable research tools with respect to allowing researchers to test the efficacy of such drugs in treating diseases associated with such amyloid deposits such as Alzheimer's disease. However, it should be pointed out that there are six known instances of disease-associated amyloid deposits in which the nature of the precursor protein for the amyloid protein is known: for primary amyloidosis, the source is an immunoglobulin light chain; for secondary amyloidosis, the precursor is amyloid A protein; for familial amyloid polyneuropathy and senile cardiac amyloidosis, prealbumin also known as transthyreitin or a variant thereof; for medullary carcinoma of thyroid, a procalcitonin fragment; and for hereditary cerebral hemorrhage, gamma-trace fragment which has been shown to be cystatin C. (See, e.g., Glenner, G. *New England Journal of Medicine* (1980) 302:1283; Sletton, K., et al., *Biochem J* (1981) 195:561; Benditt, et al., *FEBS Lett* (1971) 19:169; Sletton, K., et al., *Eur J Biochem* (1974) 41:117; and Sletton, K., et al., *J Exp Med* (1976) 143:993). The foregoing is a partial list and there are at least a number of additional references with regard to procalcitonin fragment as a precursor for the amyloid of the thyroid carcinoma. Alternatively, or additionally, such a precursor for β-amyloid core protein may be produced in the brain or elsewhere and is specifically deposited in the brain.

The transgenic animals and specifically transgenic mammals of the present invention can be used in determining the efficacy of a variety of drugs in the treatment of a variety of diseases (including those indicated above) which diseases are associated with β-amyloid deposits in the brain. Comparative drug testing protocols known to those skilled in the art can be used in connection with the transgenic mammals of the invention in order to test drugs.

Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most prevalent (Price, D. L., et al., *Drug Development Research* (1985) 5:59-68). Plaques are also seen in the brains of aged Down's Syndrome patients who develop Alzheimer's disease. The transgenic animals of the present invention can be used in connection with determining the efficacy of all types of drugs used in connection with the treatment of diseases associated with amyloid deposits, i.e., Alzheimer's Disease, (Dutch) hereditary cerebral hemorrhage with amyloidosis, and Down's Syndrome.

While preferred embodiments of making and using the invention have been described, it will be appreciated that various changes and modifications can be made without departing from the invention.

8. Deposits

The following cultures have been deposited with the American Type Culture Collection (ATCC), Rockville, Md., USA for patent purposes. Bacteriophage phages λSM2, λSM2W9, and λAPCP168i4 and plasmid pNSE-β-APP751 were deposited under the conditions specified by the Budapest Treaty on the International Recognition of the Deposit of Microorganisms (Budapest Treaty).

| Culture | Accession No. | Deposit Date |
|---|---|---|
| λSM2 | 40279 | 13 November 1986 |
| SM2W4 | 40299 | 29 December 1986 |
| SM2W3 | 40300 | 29 December 1986 |
| λSM2W9 | 40304 | 29 January 1987 |
| λACPC168i4 | 40347 | 1 July 1987 |
| pNSE-β-APP751 | 75012 | 22 May 1991 |

Availability of the deposited strains is not to be construed as a license to practice the invention in contravention of the rights granted under the authority of any government in accordance with its patent laws.

What is claimed is:

1. A transgenic mouse whose cells contain a DNA sequence, comprising:
   nerve tissue specific promoter; and
   a DNA sequence which encodes a β-amyloid precursor protein selected from the group consisting of A751 and A770,
   wherein the promoter and DNA sequence which encodes the precursor protein are operatively linked to each other and integrated in the genome of the mouse and expressed to form β-amyloid protein deposits in the brain of the mouse.

2. The transgenic mouse of claim 1, wherein the promoter is a neuronal specific enolase promoter.

3. The transgenic mouse of claim 1, wherein the promoter is rat neuronal specific enolase promoter.

4. A transgenic mouse whose cells contain a DNA sequence, comprising:
   a nerve tissue specific promoter, wherein the promoter is rat neuronal specific enolase promoter; and
   a DNA sequence which encodes β-amyloid precursor protein A751,
   wherein the promoter and DNA sequence which encodes the precursor protein are operatively linked to each other and integrated in the genome of the mouse and expressed to form β-amyloid protein deposits in the brain of the mouse.

* * * * *